US009303122B2

(12) United States Patent
Kataoka et al.

(10) Patent No.: US 9,303,122 B2
(45) Date of Patent: Apr. 5, 2016

(54) CHARGE CONVERSIONAL TERNARY POLYPLEX

(71) Applicant: THE UNIVERSITY OF TOKYO, Tokyo (JP)

(72) Inventors: Kazunori Kataoka, Tokyo (JP); Yan Lee, Tokyo (JP); Nobuhiro Nishiyama, Tokyo (JP); Kanjiro Miyata, Tokyo (JP); Makoto Oba, Tokyo (JP); Shigehiro Hiki, Tokyo (JP); Mai Sanjo, Tokyo (JP); HyunJin Kim, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/543,091

(22) Filed: Nov. 17, 2014

(65) Prior Publication Data

US 2015/0141575 A1 May 21, 2015

Related U.S. Application Data

(63) Continuation of application No. 12/990,386, filed as application No. PCT/JP2009/058793 on Apr. 30, 2009, now abandoned.

(60) Provisional application No. 61/126,077, filed on Apr. 30, 2008.

(51) Int. Cl.

| | |
|---|---|
| ***C08G 69/48*** | (2006.01) |
| ***A61K 31/7084*** | (2006.01) |
| ***A61K 31/785*** | (2006.01) |
| ***A61K 48/00*** | (2006.01) |
| ***C08G 69/10*** | (2006.01) |
| ***C08G 69/40*** | (2006.01) |
| ***C12N 15/11*** | (2006.01) |
| ***C12N 15/88*** | (2006.01) |

(52) U.S. Cl.

CPC ............ *C08G 69/48* (2013.01); *A61K 31/7084* (2013.01); *A61K 31/785* (2013.01); *A61K 48/0041* (2013.01); *C08G 69/10* (2013.01); *C08G 69/40* (2013.01); *C12N 15/111* (2013.01); *C12N 15/88* (2013.01); *C12N 2310/14* (2013.01); *C12N 2320/32* (2013.01)

(58) Field of Classification Search

CPC ............ A61K 31/7084; A61K 31/785; A61K 48/0041; C08G 69/10; C08G 69/40; C08G 69/48; C12N 15/111; C12N 15/88; C12N 2310/14; C12N 2320/32

USPC .................................. 514/44; 525/54.2, 420

See application file for complete search history.

(56) References Cited

U.S. PATENT DOCUMENTS

| | | | | |
|---|---|---|---|---|
| 4,892,733 | A | 1/1990 | Bichon et al. | |
| 7,208,314 | B2 * | 4/2007 | Monahan et al. | .......... 435/320.1 |
| 2001/0000510 | A1 | 4/2001 | Sakurai et al. | |
| 2003/0199090 | A1 | 10/2003 | Monahan et al. | |
| 2003/0236214 | A1 | 12/2003 | Wolff et al. | |
| 2006/0204584 | A1 | 9/2006 | Harper et al. | |
| 2010/0098656 | A1 | 4/2010 | Breyne et al. | |

FOREIGN PATENT DOCUMENTS

| | | | |
|---|---|---|---|
| JP | 8-188541 | A | 7/1996 |
| JP | 8188541 | A * | 7/1996 |
| JP | 2006-501156 | A | 1/2006 |
| JP | 2008-508389 | A | 3/2008 |
| WO | WO 2006/021710 | A1 | 3/2006 |
| WO | WO 2006/090924 | A1 | 8/2006 |
| WO | WO 2006090924 | A1 * | 8/2006 |

OTHER PUBLICATIONS

Lee et al. Journal of American Chemical Society, Apr. 5, 2007, 129, pp. 5362-5363.*

Extended European Search Report issued Jul. 4, 2013, in European Patent Application No. 09738905.0.

International Search Report for PCT/JP2009/058793 mailed Jun. 9, 2009.

Lee et al., "A Protein Nanocarrier from Charge-Conversion Polymer in Response to Endosomal pH", Journal of American Chemical Society, Apr. 5, 2007, vol. 129, pp. 5362-5363.

Sanjoh et al., "pDNA/poly(L-lysine) Polyplexes Functionalized with a pH-Sensitive Charge-Conversional Poly(aspartamide) Derivative for Controlled Gene Delivery to Human Umbilical Vein Endothelial Cells," Macromol. Rapid Commun. 2010, vol. 31, pp. 1181-1186.

Sanjoh et al., "Synthesis of Novel pH-Responsive Polymers based on Poly(aspartic acid) and their Utilization as Functional Components in Synthetic Gene Career System", Kobunshi Toronkai Yokoshu, Polymer Preprints, Japan, vol. 57, No. 2, Sep. 19, 2008, pp. 4809-4810.

Sanjoh et al., "Synthesis of Novel Poly(amino-acid) Based Block Copolymers via Click Chemistry", Polymer Preprints, Abstracts, Annual Meeting of the Society of Polymer Science, Japan, vol. 57, No. 1, May 8, 2008, p. 1903.

Yan Lee et al., "A Protein Nanocarrier from Charge-Conversion Polymer in Response to Endosomal pH", Journal of American Chemical Society, Apr. 5, 2007, vol. 129, pp. 5362-5363.

* cited by examiner

*Primary Examiner* — Janet Epps-Smith

(74) *Attorney, Agent, or Firm* — Birch, Stewart, Kolasch & Birch, LLP

(57) ABSTRACT

Disclosed is a polymer composite (polyplex) that contains nucleic acid, a cationic polymer, and an anionic polymer. The anionic polymer covers the surface of the composite comprising the cationic polymer and nucleic acid, has a negative charge at neutral pH, and can change so as to have a positive charge at mildly acidic pH.

11 Claims, 16 Drawing Sheets
(7 of 16 Drawing Sheet(s) Filed in Color)

A

B

C siRNA inhibtion assay (A) and MTT assay (B) of pDET(Aco) ternary complex.

CHARGE CONVERSIONAL TERNARY POLYPLEX

CROSS-REFERENCE TO RELATED APPLICATIONS

This application is a 37 C.F.R. §1.53(b) continuation of U.S. application Ser. No. 12/990,386 filed Nov. 16, 2010, which is the National Phase of PCT International Application No. PCT/JP2009/058793 filed Apr. 30, 2009, which claims priority under 35 U.S.C. §119(e) to U.S. Provisional Application No. 61/126,077 filed Apr. 30, 2008, all of which are hereby expressly incorporated by reference into the present application.

TECHNICAL FIELD

The present invention relates to a polymer complex (polyplex) containing a nucleic acid for use as a nonviral synthetic vector capable of delivering the nucleic acid to a target cell. More particularly, the present invention relates to a charge conversional ternary polyplex comprising a nucleic acid, a cationic polymer and an anionic polymer, wherein the anionic polymer covers the surface of a complex comprising the cationic polymer and the nucleic acid.

BACKGROUND ART

DNA or RNA delivery to a target cell mediated by a nonviral synthetic vector (lipoplex and polyplex) has been widely recognized as a promising alternative method for delivery that uses a viral vector which has been confronting safety issues specific to biological properties[1]. Nonetheless, even in the case of a nonviral vector, the main concern is the conflict between the delivery efficiency and the safety issues (in particular, chemical toxicity). While most vectors having high transfection efficiency show high toxicity, vectors with low toxicity are often associated with low transfection efficiency. Behr et al. introduced a concept of endosomal escape through "proton-sponge" effect, a hypothesis proposed for polyethylenimine (PEI), into the field of gene delivery. Since then, various basicity-adjusted polycations have been developed for construction of polyplexes. However, due to the toxicity of these polycations, polyplexes are used only for limited applications[2]. One major reason for limited development of polycation is presumably that different functions, which may be opposing functions, of the polyplex are required at different stages of the delivery process. For example, a moiety having a high amine density in a polyplex is important to overcome the endosomal membrane barrier since a protonated potential of the polyplex could be a cause of endosome buffering and membrane destabilization[3]. On the contrary, the positively-charged property of a polyplex could cause non-specific interaction with a negatively-charged serum component, thereby producing a thrombus in the blood capillary. This has a risk of disturbing construction of a plasma membrane and a risk of inducing high cytotoxicity and excess immune response[4]. An example of well known practical solutions to these problems is positive charge shielding by covering the surface of the polyplex with polyanion[5] or polyethylene glycol (PEG)[6]. In this case, however, severe loss in transfection efficiency cannot be avoided primarily due to decrease in the cellular uptake and deterioration of the endosomal escape ability.

Thus, efforts have been focused on the development of a deshielding method at a certain point during the transfection process[7].

DISCLOSURE OF THE INVENTION

Accordingly, the present inventors have examined a new approach for a polyplex design that exerts both properties of high transfection activity and low toxicity by integrating a charge conversional moiety into a polyplex structure. Although maleic acid amide derivatives, i.e., cis-aconitic acid amide and citraconic acid amide, bear negative charges at neutral pH, they are rapidly degraded at weak acidity of pH 5.5 and expose the positively-charged amine[8]. Therefore, a ternary polyplex (a polyplex having pDNA/polycation/polyanion having degrading side-chain) formed by the present inventors by covering the surface of a positively-charged polyplex with a polymer derived from degrading amide, by which the ternary polymer maintains neutrally- to negatively-charged properties outside the cell. On the other hand, in the acidic environment of endosomes, the charge conversional moieties are expected to charge positively and promote endosomal escape of the polyplex owing to membrane disruption. This scheme is illustrated in FIG. 1.

The present invention has an objective of providing a polymer that is negatively charged outside the cell but that undergoes charge conversion and positively charged once entering the endosome. The present invention also has an objective of providing a complex (polyplex) comprising the polymer, namely a ternary polyplex which overcomes the problem (dilemma) existing between gene transfection efficiency and safety and which can fulfill low toxicity and high gene transfection efficiency.

In order to solve the above-described problems, the present inventors have gone through keen examination. As a result, they found that a polymer obtained by causing a polycation to react with citraconic anhydride or cis-aconitic anhydride is negatively charged under a neutral condition but its charge is converted to give a cation under an acidic condition, and therefore the polymer shows low toxicity and high gene transfection efficiency, thereby accomplishing the present invention.

Thus, the present invention is an anionic polymer represented by the following Formula (1).

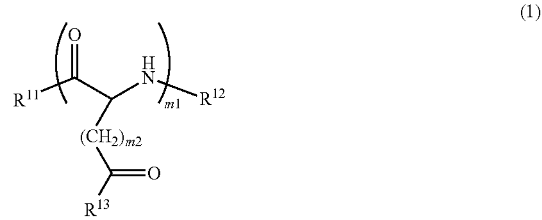

(1)

[wherein, $R^{11}$ and $R^{12}$ independently represent a hydrogen atom or an optionally substituted linear or branched alkyl group with a carbon number of 1-12, $R^{13}$ represents a conjugate of a residue derived from an amine compound having a primary amine, and a compound represented by Formula (I) below:

(I)

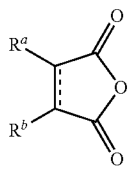

(wherein, $R^a$ and $R^b$ independently represent a hydrogen atom, or an optionally substituted alkyl group, alkenyl group, cycloalkyl group, aryl group, aralkyl group, acyl group, heterocyclic group, heterocyclic alkyl group, hydroxy group, alkoxy group or aryloxy group, and $R^a$ and $R^b$ may bind to each other to form an aromatic ring or a cycloalkyl ring with the carbon atoms to which they are each bound, where the binding between the carbon atoms to which $R^a$ and $R^b$ are each bound is either a single bond or a double bond) or a derivative thereof, m1 represents an integer of 10-500, and m2 represents an integer of 1-5].

For an anionic polymer of the present invention, examples of the residue derived from an amine compound having a primary amine include: a group represented by General Formula (11) below:

$$—NH—(CH_2)_r—X^{11} \quad (11)$$

(wherein, $X^{11}$ represents an amine compound residue derived from primary, secondary or tertiary amine compound or quaternary ammonium salt, and r represents an integer of 0-5); and a group represented by General Formula (12) below:

$$—[NH—(CH_2)_{s1}]_{t1}—X^{12} \quad (12)$$

(wherein, $X^{12}$ is synonymous with $X^{11}$, and s1 and t1, independently from each other and independently between $[NH—(CH_2)_{51}]$ units, represent integers of 1-5 and 2-5, respectively), and preferably a group represented by —NH—$NH_2$ or —NH—$(CH_2)_2$—NH—$(CH_2)_2$—$NH_2$.

Moreover, for an anionic polymer of the present invention, the compound represented by Formula (I) above may be, for example, at least one type of the compounds represented by Formulae (Ia)-(Ig) below.

(Ia)

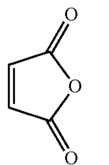

(Ib)

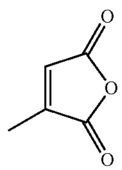

(Ic)

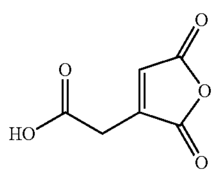

-continued (Id)

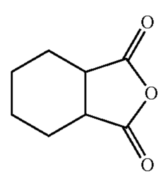

(Ie)

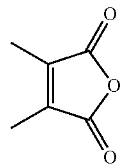

(If)

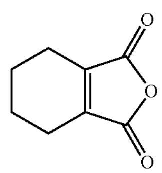

(Ig)

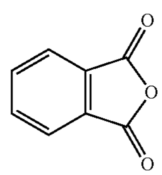

Furthermore, the present invention also provides a polymer complex comprising a nucleic acid, a cationic polymer and the above-mentioned anionic polymer.

For the polymer complex of the present invention, examples of the nucleic acid include plasmid DNA and siRNA.

Examples of the cationic polymer include any compound selected from the group consisting of:

a compound represented by the following Formula (2):

(2)

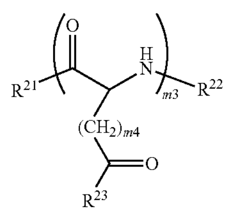

[wherein, $R^{21}$ and $R^{22}$ independently represent a hydrogen atom or an optionally substituted linear or branched alkyl group with a carbon number of 1-12, $R^{23}$ represents a residue derived from an amine compound having a primary amine, m3 represents an integer of 10-500, and m4 represents an integer of 1-5];

a compound represented by the following Formula (3):

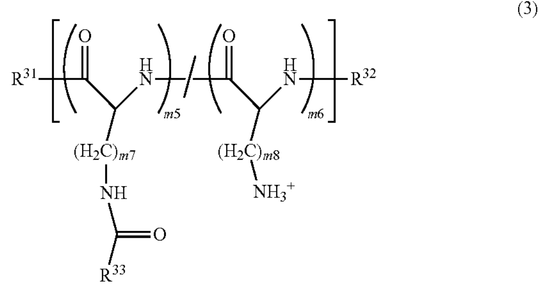

[wherein, $R^{31}$ and $R^{32}$ are synonymous with $R^{21}$ and $R^{22}$, respectively, $R^{33}$ represents an optionally substituted saturated or unsaturated linear or branched aliphatic hydrocarbon group or steroloxycarbonyl group with a carbon number of 11-27, m5 and m6 independently represent an integer of 0-500 (provided that the sum of m5 and m6 is an integer of 10-500), m7 represents an integer of 1-5, m8 represents an integer of 1-5, and the sign "/" indicates that the sequential order of the (m5+m6) numbers of monomer units on both sides of the sign are arbitrary];

a compound represented by the following Formula (4):

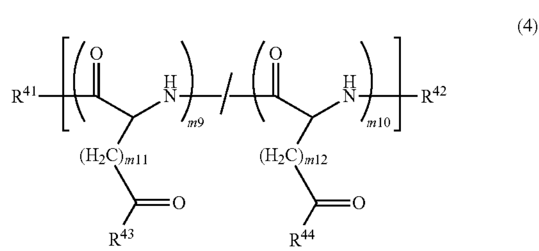

[wherein, $R^{41}$ and $R^{42}$ are synonymous with $R^{21}$ and $R^{22}$, respectively, $R^{43}$ is synonymous with $R^{33}$, $R^{44}$ is synonymous with $R^{23}$, m9 and m10 are synonymous with m5 and m6, respectively, m11 and m12 are synonymous with m7 and m8, respectively, and sign "/" is synonymous with the same above]; and a compound represented by the following Formula (5):

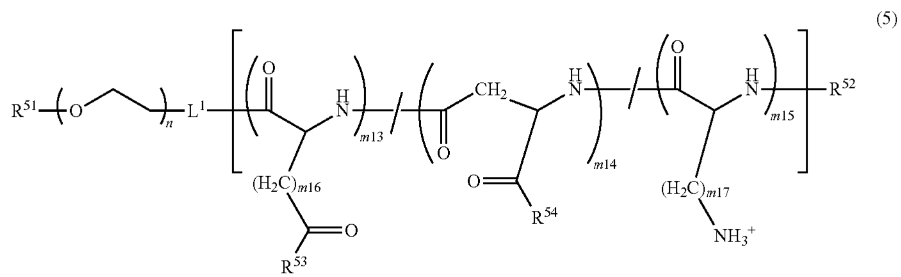

[wherein, $R^{51}$ and $R^{52}$ are synonymous with $R^{21}$ and $R^{22}$, respectively, $R^{53}$ and $R^{54}$ are synonymous with $R^{23}$, $L^1$ represents NH, CO, a group represented by General Formula (13) below:

$$—(CH_2)_{p1}—NH— \quad (13)$$

(wherein, p1 represents an integer of 1-6) or a group represented by General Formula (14) below:

$$-L^{2a}-(CH_2)_{q1}-L^{3a}- \quad (14)$$

(wherein, $L^{2a}$ represents OCO, OCONH, NHCO, NHCOO, NHCONH, CONH or COO, $L^{3a}$ represents NH or CO, and q1 represents an integer of 1-6), m13, m14 and m15 independently represent an integer of 0-500 (provided that the sum of m13, m14 and m15 is an integer of 10-500), m16 and m17 are synonymous with m7 and m8, respectively, n represents an integer of 0-500, and the sign "/" indicates that the sequential order of the (m13+m14+m15) numbers of monomer units on both sides of the sign are arbitrary].

Furthermore, the present invention also provides a device or a kit for delivering a nucleic acid into a cell, comprising the polymer complex.

In a preferred embodiment of a polymer complex (polyplex) of the present invention, an anionic polymer covers the surface of a complex of a cationic polymer and a nucleic acid. The anionic polymer can change its charge from negative at neutral pH to positive at weak acidic pH.

A specific example of such an anionic polymer includes a polymer (specifically, "pAsp (DET-Aco)") shown in FIG. 2A(c).

The present invention can provide a charge conversional ternary polyplex that is charged negatively under a neutral condition but its charge is converted to give a cation under an acidic condition.

In the field of gene vector studies, transfection into a toxicity-sensitive primary cell such as HUVEC is extremely difficult. A polyplex of the present invention is capable of delivering a nucleic acid such as DNA or siRNA to such types of cells in a highly efficient manner without evoking toxicity. Medically speaking, major drawbacks of nucleic acid delivery include low efficiency, high toxicity and instability in the blood. The charge conversional ternary polyplex of the present invention has very low toxicity since it is negatively charged outside the cell and thus is extremely useful as a gene vector in vivo.

BRIEF DESCRIPTION OF THE DRAWINGS

The patent or application file contains at least one color drawing. Copies of this patent or patent application publication with color drawing will be provided by the USPTO upon request and payment of the necessary fee.

(A) Structures of polycations: (a) pAsp(DET), (b) pAsp (EDA-Suc) (non-charge-conversional polyanion) and (c) pAsp(DET-Aco) (charge conversional polyanion).

(B) Charge conversion of ternary polyplex (DNA/pAsp(DET)/pAsp(DET-Aco)).

(C) Change in hydrodynamic diameter of a ternary polyplex. White circles (○) represent the results at pH 5.5 while black circles (●) represent the results at pH 7.4.

Figure 3:
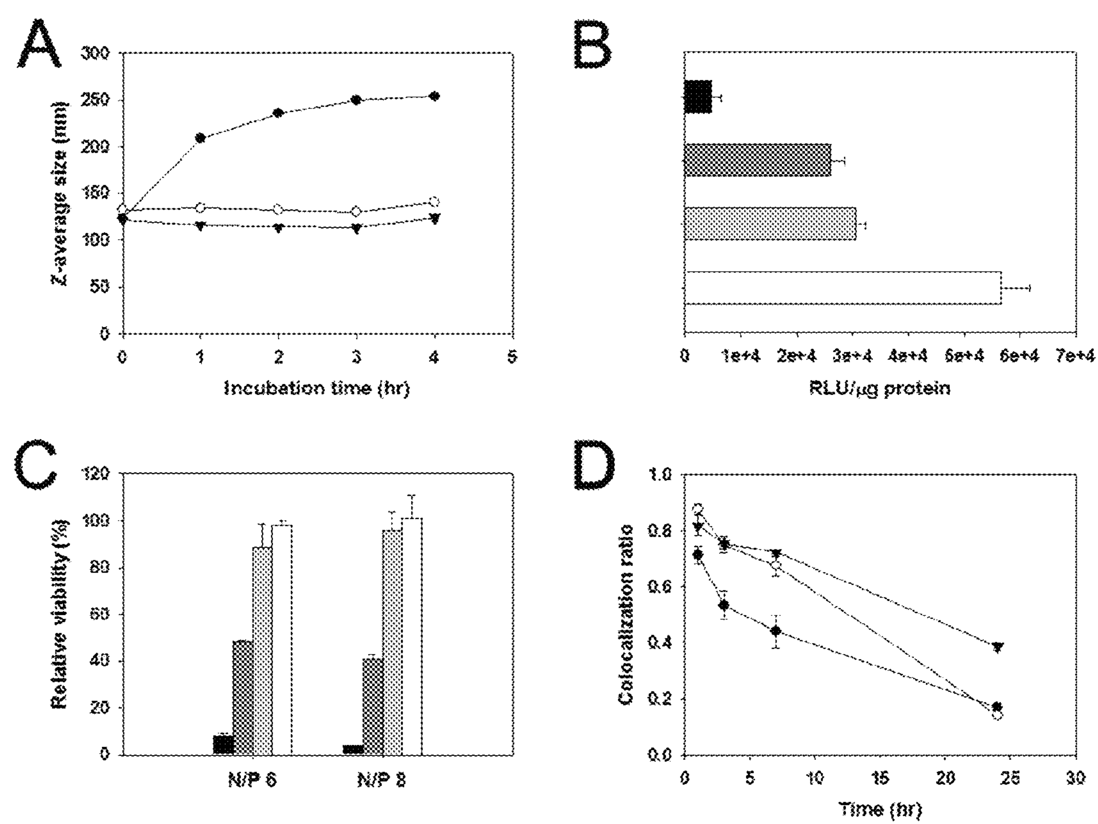

FIG. 3 shows the results from analyzing the functions of polyplexes.

(A) Stability of the polyplexes in a BSA solution.

(B) Transfection activities of various vectors.

(C) Relative viabilities of HUVEC transfected with various vectors.

(D) Colocalization ratio of red fluorescence of Cy5-labeled DNA and green fluorescence of LysoTracker Green.

Each error bar indicates standard error. ExGen 500 (black bar); pAsp(DET) polyplex (● and dark gray bar); pAsp(EDA-Suc) ternary polyplex (▼ and gray bar); and pAsp(DET-Aco) ternary polyplex (○ and white bar).

Figure 4:
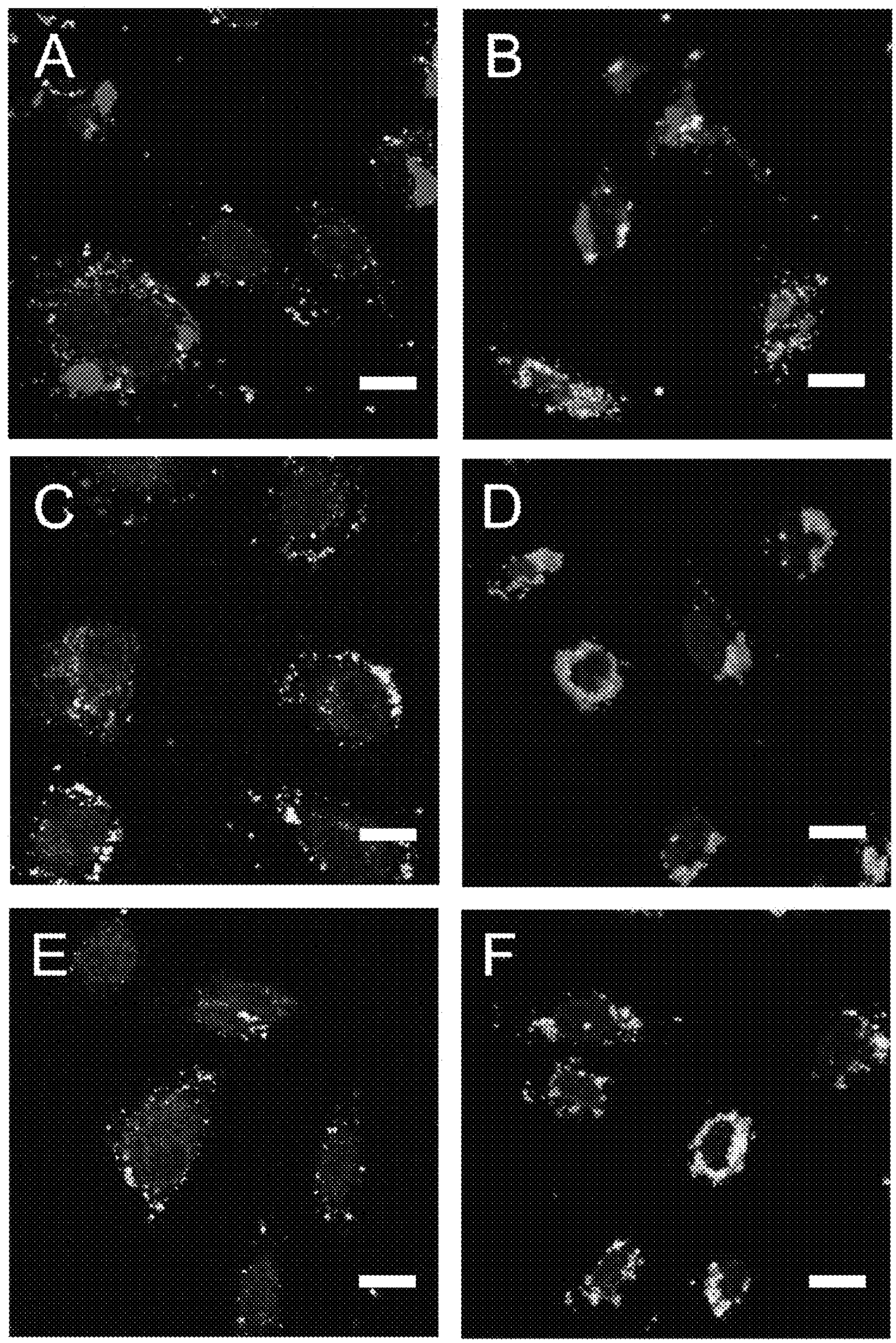

FIG. 4 shows the results from observation of HUVEC with a confocal microscope.

(A) and (B) are CLSM images of HUVEC transfected with pAsp(DET) polyplex.

(C) and (D) are CLSM images of HUVEC transfected with pAsp(DET-Aco) ternary polyplex.

(E) and (F) are CLSM images of HUVEC transfected with pAsp(EDA-Suc) ternary polyplex.

(A), (C) and (E) are images obtained 3 hours after transfection while (B), (D) and (F) are images obtained 24 hours after transfection. Cy5 (red)-labeled plasmid DNA was used. Cell nuclei were stained with Hoechst 33342 (blue) while late endosomes and lysosomes were stained with LysoTracker Green (green). Each scale bar measures 20 μm.

Figure 5:
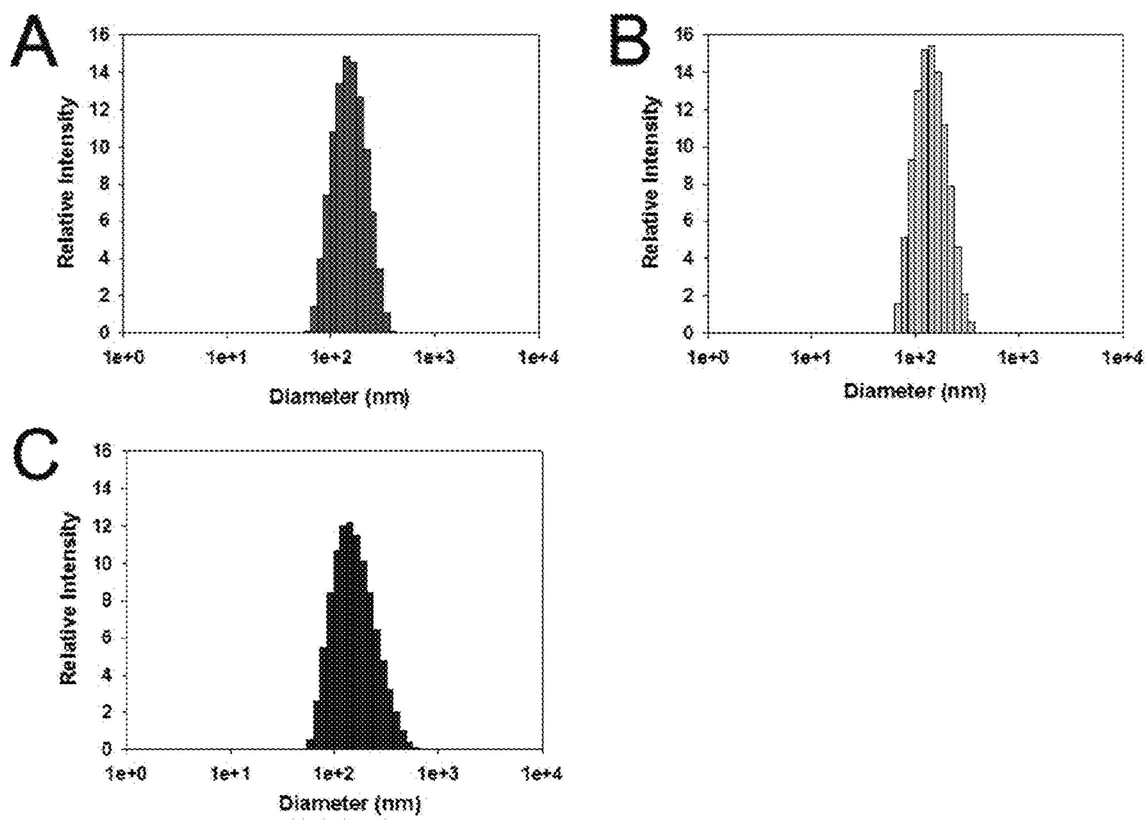

FIG. 5 shows the size distribution of each polyplex.

Size distributions of DNA/pAsp(DET) polyplex (N/P ratio=4) (A), pAsp(DET)/pAsp(DET-Aco) complex (pAsp(DET-Aco)/pAsp(DET)=2) (B) and (DNA/pAsp(DET)/pAsp(DET-Aco) ternary polyplex (N/P ratio=4; pAsp(DET-Aco)/pAsp(DET)=2) (C).

Figure 6:
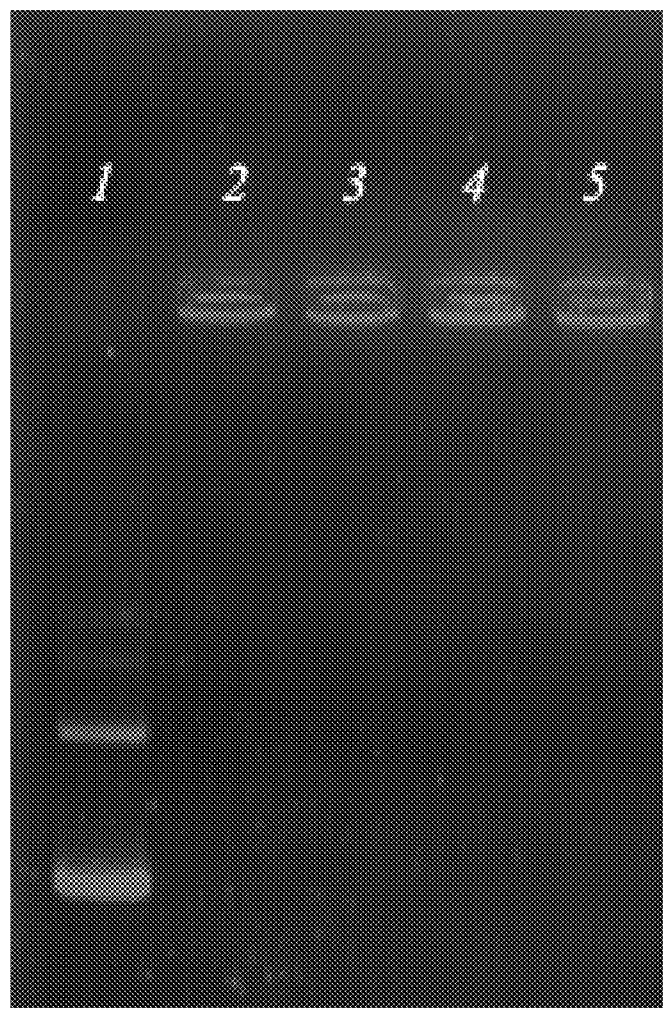

FIG. 6 shows the results from gel retardation assay of polyplexes.

Lane 1: pDNA only;

Lane 2: pDNA/pAsp(DET) polyplex (N/P ratio 4);

Lane 3: pDNA/pAsp(DET)/pAsp(DET-Aco) (N/P=4, pAsp(DET-Aco)/pAsp(DET)=2);

Lane 4: pDNA/pAsp(DET)/pAsp(DET-Aco) (N/P=6, pAsp(DET-Aco)/pAsp(DET)=2);

Lane 5: pDNA/pAsp(DET)/pAsp(DET-Aco) (N/P=8, pAsp(DET-Aco)/pAsp(DET)=2).

Figure 7:
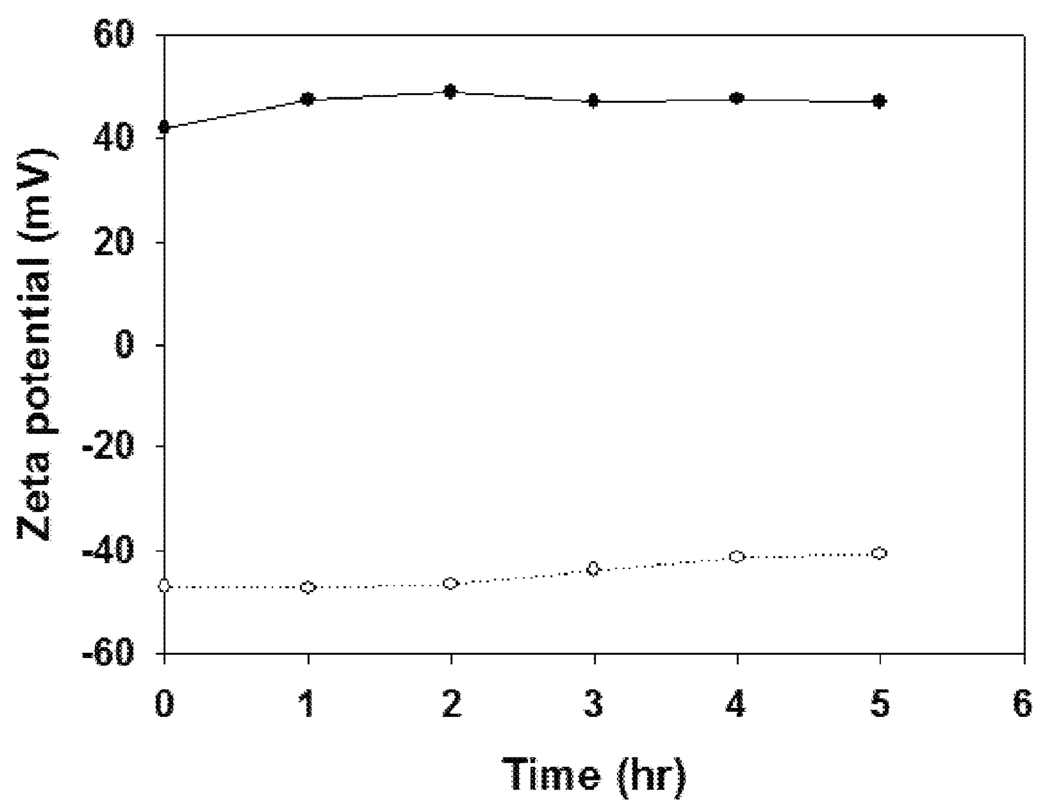

FIG. 7 shows changes in zeta potentials of pAsp(DET) polyplex (●) and pAsp(EDA-Suc) (○) ternary polyplex at pH 5.5.

Figure 8:
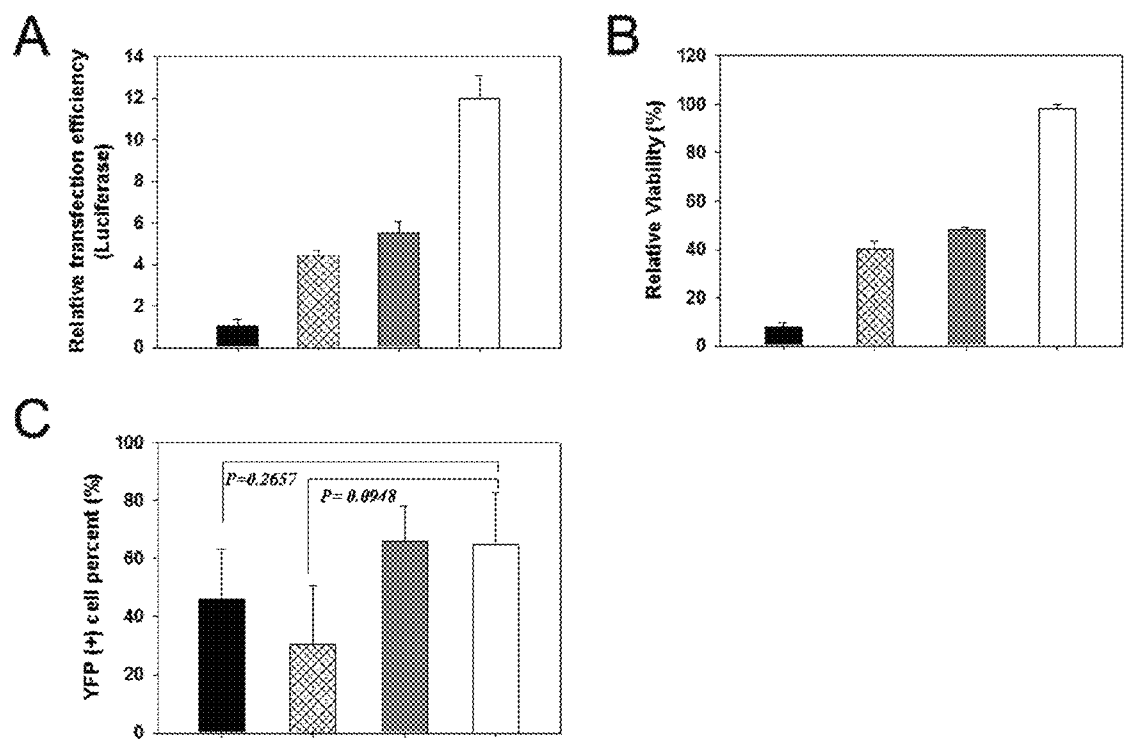

FIG. 8 shows comparison of transfection efficiency and toxicity by luciferase and Venus (YFP) transfection assays.

(A) Relative transfection efficiency with respect to luciferase activity (RLU/μg protein).

(B) Relative cell viability by MTT assay.

(C) Relative Venus (YFP) expression calculated by Venus (+) cell count.

Black bar; ExGen 500 (Fermentas, Canada)

Hatching bar; Lipofectamine 2000 (Invitrogen, USA)

Dark gray bar; pAsp(DET) polyplex

White bar; pAsp(DET-Aco) ternary polyplex.

Each error bar indicates standard deviation.

Figure 9:
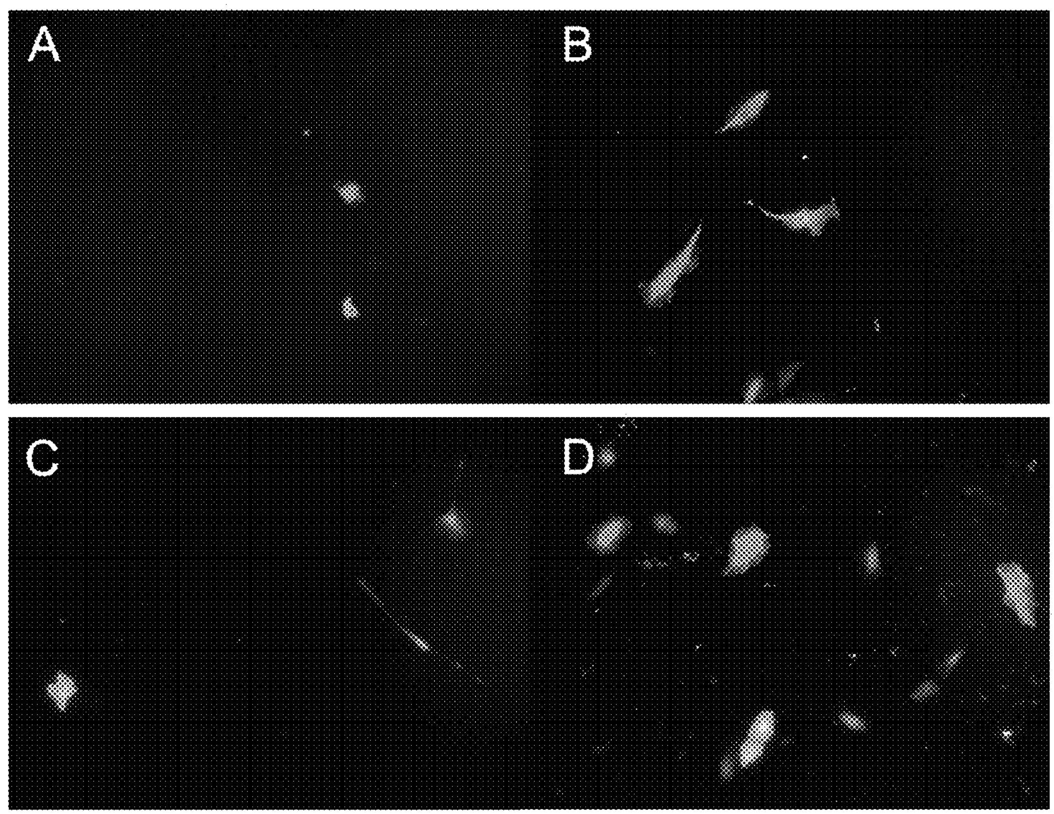

FIG. 9 shows results of Venus (YFP) transfection into HUVEC using various transfection reagents.

(A) ExGen 500, (B) Lipofectamine 2000, (C) pAsp(DET) polyplex and (D) pAsp(DET-Aco) ternary polyplex.

Figure 10:
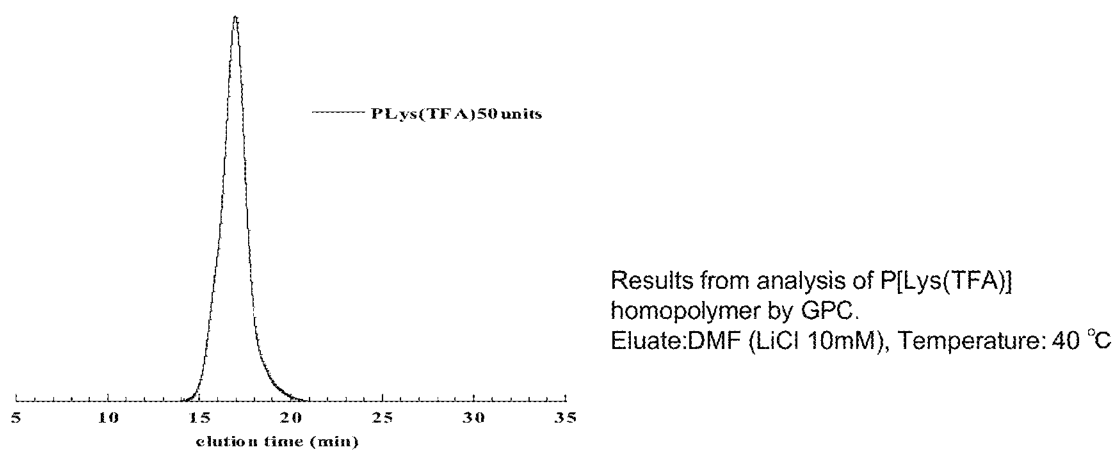

FIG. 10 shows results from an analysis of P[Lys(TFA)] homopolymer by gel permeation chromatography.

Figure 11:
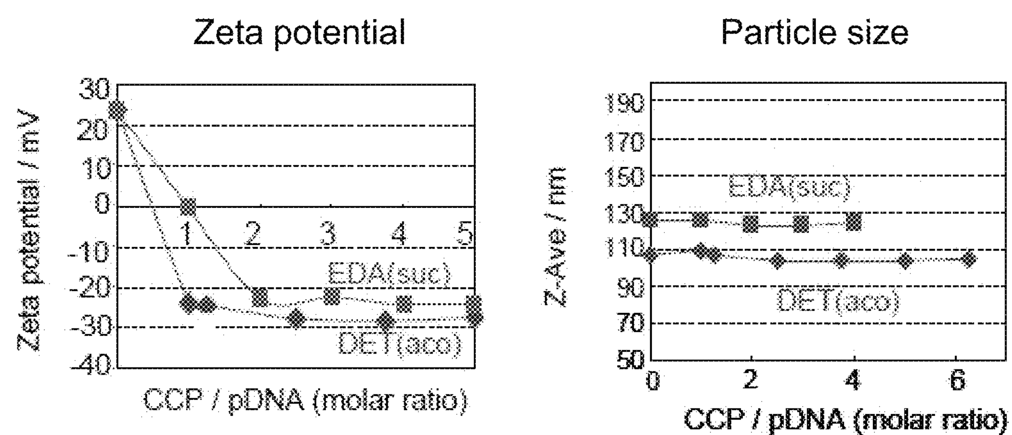

FIG. 11 shows results from physicochemical assessments (particle size and zeta potential measurements) of pDNA/PLL polyplex and a ternary polyplex.

Figure 12:
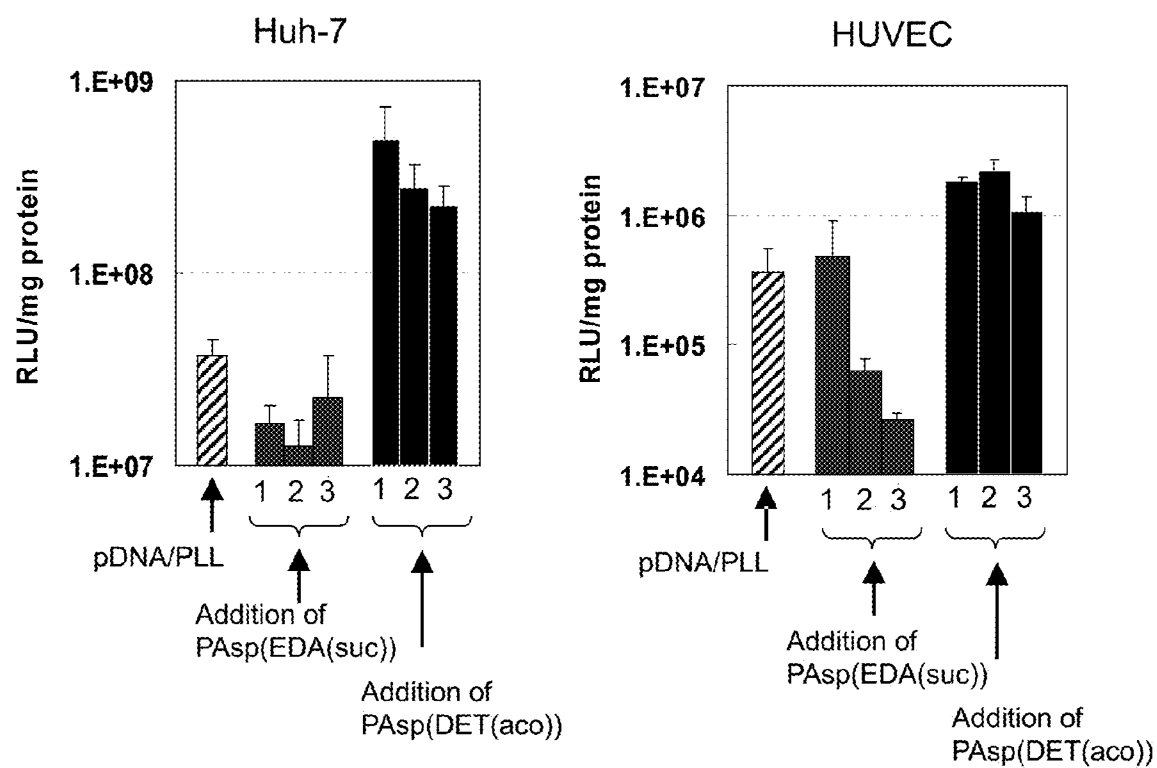

FIG. 12 shows results from testing gene expression activity with the use of a ternary polyplex of the present invention.

Figure 13:
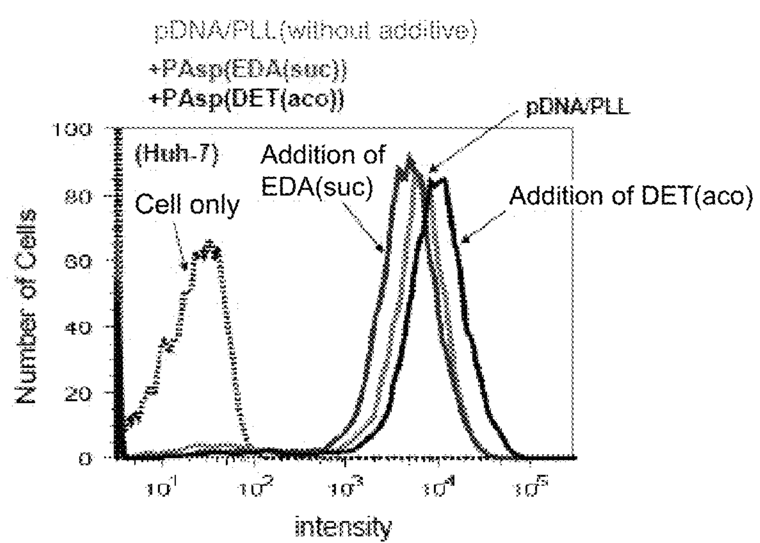

FIG. 13 shows results from analysis with respect to intracellular uptake of a ternary polyplex of the present invention with a flow cytometer.

Figure 14:
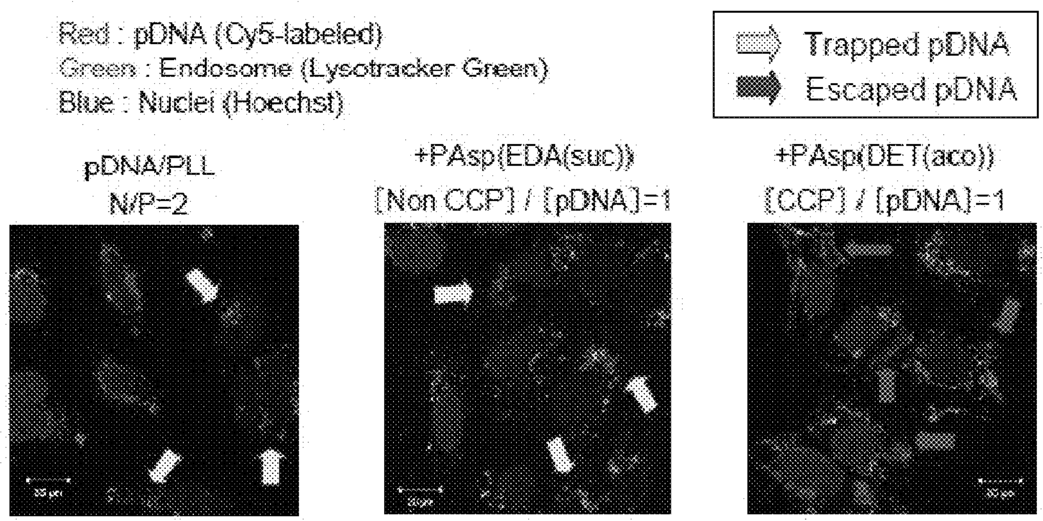

FIG. 14 shows results from observation with a confocal laser microscope.

Figure 15:
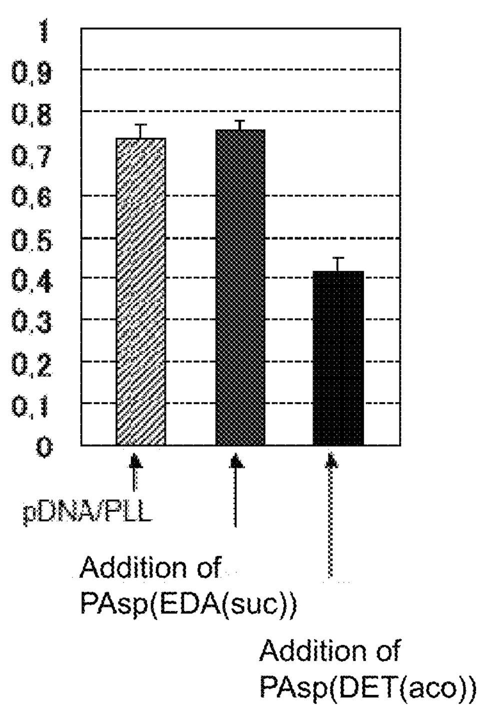

FIG. 15 shows results from a quantitative assessment of polyplexes trapped in endosomes.

Figure 16:
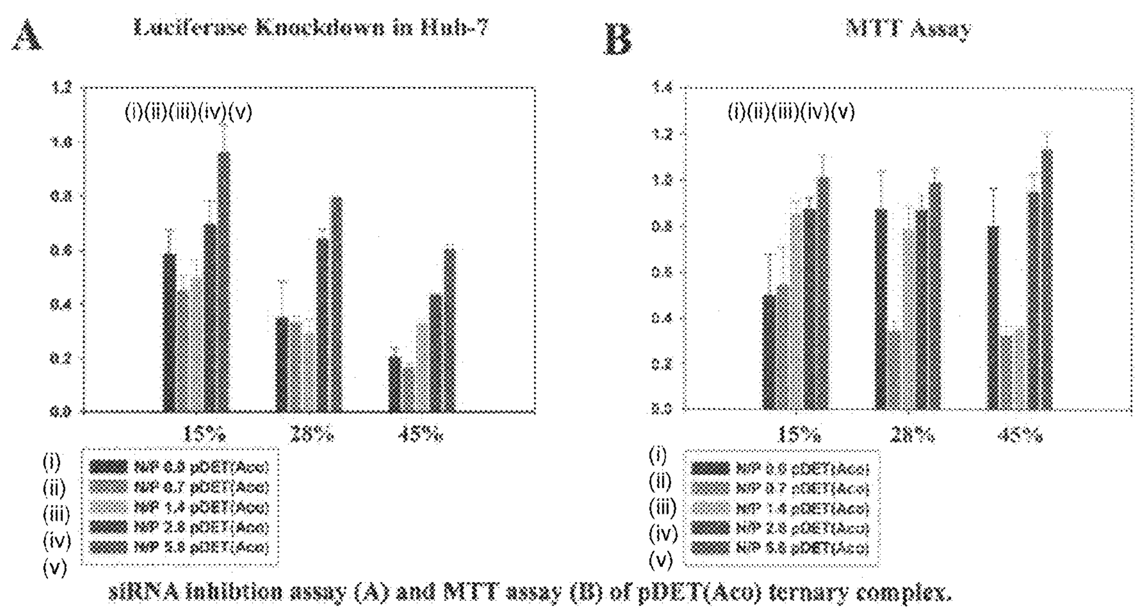

FIG. 16 shows the effect of siRNA-bearing ternary polyplexes on knocking down luciferase gene and cytotoxicity associated with siRNA transfection.

MODES FOR CARRYING OUT THE INVENTION

Hereinafter, the present invention will be described in detail. The following descriptions, however, are not intended to limit the scope of the present invention. It should be understood that the following embodiments may be altered or modified without departing from the spirit of the present invention.

The present specification incorporates the content described in the specification of U.S. Provisional Application No. 61/126,077 (filed on Apr. 30, 2008) to which the present application claims priority.

Furthermore, all of the documents and publications cited herein are incorporated herein by reference in their entirety for any purposes.

The present invention is a polymer complex (polyplex) comprising a nucleic acid, a cationic polymer and an anionic polymer, wherein the anionic polymer is negatively charged at neutral pH and its charge is altered to positive at weak acidic pH. The present invention also provides an anionic polymer that constitutes the above-mentioned polymer complex.

1. Anionic Polymer

An anionic polymer of the present invention is represented by the following Formula (1) and is used as a charge conversional polymer.

(1)

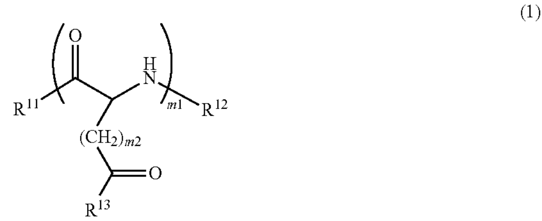

[wherein, $R^{11}$ and $R^{12}$ independently represent a hydrogen atom or an optionally substituted linear or branched alkyl group with a carbon number of 1-12, $R^{13}$ represents a conjugate of a residue derived from an amine compound having a primary amine and a compound represented by Formula (I) below:

(I)

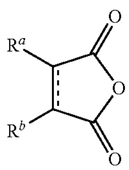

(wherein, $R^a$ and $R^b$ independently represent a hydrogen atom, or an optionally substituted alkyl group, alkenyl group, cycloalkyl group, aryl group, aralkyl group, acyl group, heterocyclic group, heterocyclic alkyl group, hydroxy group, alkoxy group or aryloxy group, and $R^a$ and $R^b$ may bind to each other to form an aromatic ring or a cycloalkyl ring with the carbon atoms to which they are bound, where the binding between the carbon atoms to which $R^a$ and $R^b$ are bound is either a single bond or a double bond) or a derivative thereof, m1 represents an integer of 10-500, and m2 represents an integer of 1-5].

For the anionic polymer of the present invention, examples of the residue derived from an amine compound having a primary amine include groups represented by General Formulae (11) or (12) below.

$$—NH—(CH_2)_r—X^{11} \quad (11)$$

(wherein, $X^{11}$ represents an amine compound residue derived from primary, secondary or tertiary amine compound or quaternary ammonium salt, and r represents an integer of 0-5)

$$—[NH—(CH_2)_{s1}]_{t1}—X^{12} \quad (12)$$

(wherein, $X^{12}$ is synonymous with $X^{11}$, and s1 and t1, independently from each other and independently between $[NH—(CH_2)_{s1}]$ units, represent integers of 1-5 and 2-5, respectively).

According to the present invention, a residue derived from an amine compound having a primary amine is preferably one represented by $—NH—NH_2$ or $—NH—(CH_2)_2—NH—(CH_2)_2—NH_2$.

According to the present invention, the compound represented by Formula (I) above may be, for example, at least one type of the compounds represented by Formulae (Ia)-(Ig) below.

(Ia)

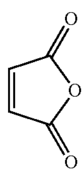

maleic anhydride (pH 3)

(Ib)

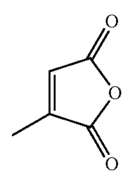

citraconic anhydride (pH 5.5)

-continued (Ic)

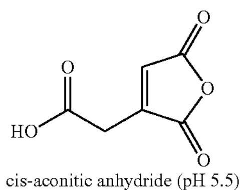

cis-aconitic anhydride (pH 5.5)

(Id)

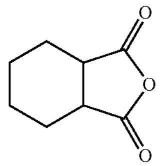

1,2-cyclohexanedicarboxylic anhydride (pH 5.5)

(Ie)

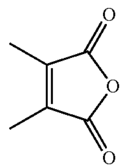

dimethylmaleic anhydride (pH 2)

(If)

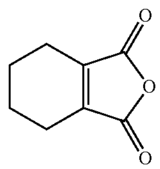

3,4,5,6-tetrahydrophthalic anhydride (pH 2)

(Ig)

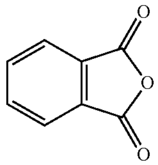

phthalic anhydride (pH 3)

A preferable example of an anionic polymer contained in the polyplex of the present invention includes pAsp(DET-Aco), where the structure of pAsp(DET-Aco) is a polymer having an anionic side-chain by binding an N'-cis-aconityl group to an amino group at the end of the side-chain of a cationic polymer pAsp(DET) (that is, an amino acid polymer obtained by binding an ethylenediamine unit to an aspartate backbone). pAsp(DET-Aco) may be synthesized by causing a primary amino group of a hydrophobic group (e.g., PLL) to react with a compound represented by Formula I (for example, cis-aconityl anhydride).

Binding between a residue derived from an amine compound having a primary amine and a compound represented by Formula (I) or a derivative thereof may be obtained, for example, by binding (covalently linking) the compound represented by Formula (I) above and the amino group of the amine compound to give a structure represented by Formula (I') below. Here, such a derivative refers to any compound derived from a compound having General Formula (I) above as a fundamental backbone. For example, such a derivative may be a compound obtained by replacing COOH of compound (Ic) with an alkyl group, a compound obtained by replacing a methyl group of compound (Ib) or (Ie) with other alkyl group, or a compound obtained by replacing an aromatic ring or a cycloalkyl ring with at least one halogen atom.

In Formula (I), a substituent group may be a saturated or unsaturated acyclic or cyclic hydrocarbon group. In the case of an acyclic hydrocarbon group, it may be either linear or branched. Examples of the hydrocarbon group include a $C_1$-$C_{20}$ alkyl group, a $C_2$-$C_{20}$ alkenyl group, a $C_4$-$C_{20}$ cycloalkyl group, a $C_6$-$C_{18}$ aryl group, a $C_6$-$C_{20}$ aralkyl group, a $C_1$-$C_{20}$ alkoxy group and a $C_6$-$C_{18}$ aryloxy group.

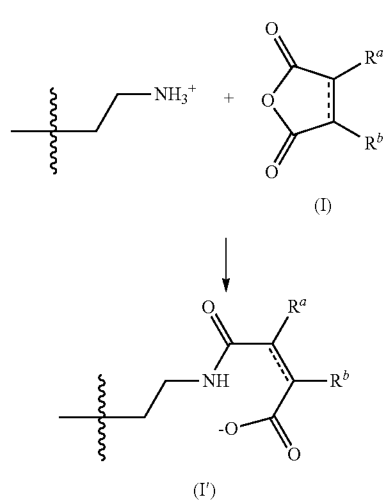

As to this binding, for example, when the compound represented by Formula (I) above is a compound represented by Formula (Ib) and (Ic) above, the structure represented by Formula (I') above after the binding will be as follows.

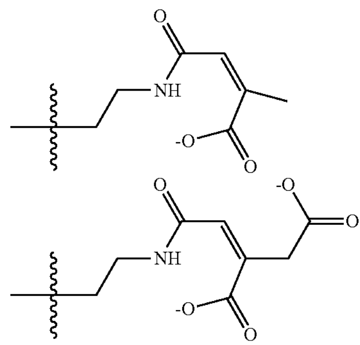

2. Cationic Polymer

A specific cationic polymer as a constituent of a complex of the present invention is a cationic polymer having at least partially a polycation moiety.

According to the present invention, a cationic polymer (polycation) is not limited to the above-mentioned pAsp (DET) (comprising pAsp(DET), i.e., a fundamental backbone of pAsp(DET-Aco) above). Any polypeptides that are known to have a cationic group in the side-chain may be comprised. These may be used for carrying out the present invention in the same manner as pAsp(DET) by technical knowledge common for those skilled in the art. The cationic group used herein is not limited to a group which has already been rendered cationic with a coordinated hydrogen ion but it may also comprise a group that will be cationic once it gains a hydrogen ion. A polypeptide having a cationic group in the side-chain comprises polypeptides obtained through peptide bond of known amino acids having basic side-chains (lysine, arginine, histidine, etc.) as well as polypeptides obtained through peptide bond of any amino acid and subsequent substitution in the side-chain to have a cationic group.

3. Monopolymer

Examples of a cationic polymer (monopolymer) include compounds represented by the following Formulae (2)-(4):

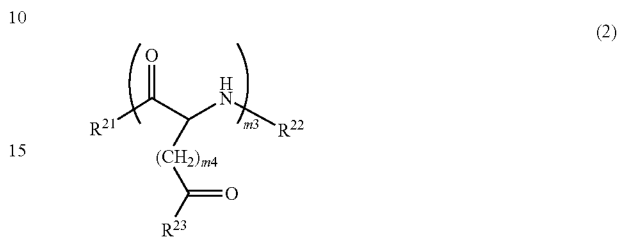

[wherein, $R^{21}$ and $R^{22}$ independently represent a hydrogen atom or an optionally substituted linear or branched alkyl group with a carbon number of 1-12, $R^{23}$ represents a residue derived from an amine compound having a primary amine, m3 represents an integer of 10-500, and m4 represents an integer of 1-5];

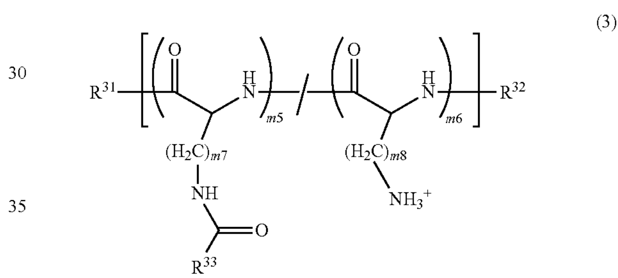

[wherein, $R^{31}$ and $R^{32}$ are synonymous with $R^{21}$ and $R^{22}$, respectively, $R^{33}$ represents an optionally substituted saturated or unsaturated linear or branched aliphatic hydrocarbon group or steroloxycarbonyl group with a carbon number of 11-27, m5 and m6 independently represent an integer of 0-500 (provided that the sum of m5 and m6 is an integer of 10-500), m7 represents an integer of 1-5, m8 represents an integer of 1-5, and the sign "/" indicates that the sequential order of the (m5+m6) numbers of monomer units on both sides of the sign are arbitrary]; and

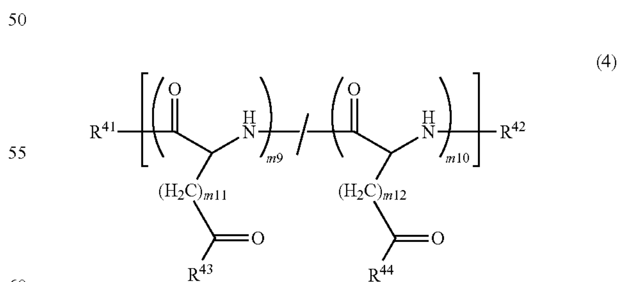

[wherein, $R^{41}$ and $R^{42}$ are synonymous with $R^{21}$ and $R^{22}$, respectively, $R^{43}$ is synonymous with $R^{33}$, $R^{44}$ is synonymous with $R^{23}$, m9 and m10 are synonymous with m5 and m6, respectively, m11 and m12 are synonymous with m7 and m8, respectively, and the sign "/" is synonymous with the same above].

In General Formula (2), $R^2$ containing a cationic group represents a residue derived from an amine compound having a primary amine. Examples of —$R^{23}$ group include groups represented by General Formulae (22) and (23) below, among which a group represented by General Formula (23) below is preferable:

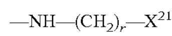

$$—NH—(CH_2)_r—X^{21} \quad (22)$$

[wherein, $X^{21}$ represents a primary, secondary or tertiary amine compound or an amine compound residue derived from quaternary ammonium salt, and r represents an integer of 0-5]; and $$—[NH—(CH_2)_{s2}]_{t2}—X^{22} \quad (23)$$

[wherein, $X^{22}$ represents a primary, secondary or tertiary amine compound or an amine compound residue derived from quaternary ammonium salt, and s2 and t2, independently from each other and independently between [NH—$(CH_2)_{s2}$] units, represent integers of 1-5 (preferably 2) and 2-5 (preferably 2), respectively].

In General Formulae (22) and (23), preferable examples of —$X^{21}$ and —$X^{22}$ groups (amine compound residues) at the terminals include —$NH_2$, —NH—$CH_3$, —$N(CH_3)_2$ and groups represented by Formula (i)-(viii) below, among which —$NH_2$ is particularly preferable. In Formula (vi) below, examples of Y include a hydrogen atom, an alkyl group (with a carbon number of 1-6) and an aminoalkyl group (with a carbon number of 1-6).

(i)

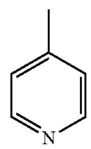

(ii)

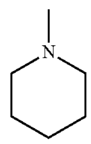

(iii)

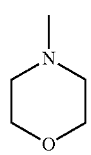

(iv)

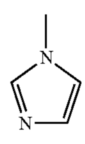

(v)

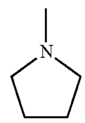

-continued (vi)

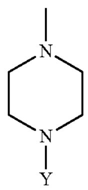

(vii)

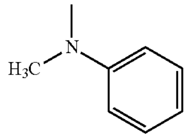

(viii)

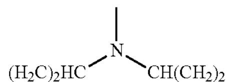

Specifically, —$R^{23}$ in General Formula (2) is particularly preferably "—NH—$NH_2$" or "—NH—$(CH_2)_2$—NH—$(CH_2)_2$—$NH_2$", among which the latter containing an ethylenediamine unit is more preferable.

In General Formula (2), m3 represents, but not limited to, an integer of 100-500, preferably 30-150 (more preferably 60-100), and m4 preferably represents, but not limited to, an integer of 1-5 (more preferably 1-2).

A saturated aliphatic hydrocarbon residue is equivalent to an alkyl group with a carbon number of 11-27, examples including, in addition to the above-mentioned alkyl group, a pentacosyl group, a hexacosyl group and a heptacosyl group. An unsaturated aliphatic hydrocarbon residue refers to a group in which 1-5 carbon-carbon single bonds in the chain of the alkyl group are replaced by carbon-carbon double bonds. Examples of an acyl group (RCO—) having such a residue (R) include, but not limited to, lauric acid (or dodecanoic acid), myristic acid (or tetradecanoic acid), palmitic acid (or hexadecane acid), palmitoleic acid (or 9-hexadecenoic acid), stearic acid (or octadecanoic acid), oleic acid, linoleic acid, linolenic acid, eleostearic acid (or 9,11,13-octadecatrienoic acid), arachidic acid, arachidonic acid, behenic acid, lignoceric acid, nervonic acid, cerotic acid and montanic acid.

According to the present invention, sterol refers to a natural, semisynthetic or synthetic compound based on a cyclopentanone hydrophenanthrene ring (C17H28), and further refers to derivatives thereof. For example, natural sterols may be, but not limited to, cholesterol, cholestanol, dihydrocholesterol, cholic acid, campesterol and cystosterol while semisynthetic or synthetic compounds thereof may be, for example, synthetic precursors of these natural products (comprising compounds in which, if necessary, a certain functional group or a part or all of hydroxy groups, if any, may be protected with a hydroxy protecting group known in the art, or a carboxyl group is protected by carboxyl protection). Furthermore, a sterol derivative may have a C1-12 alkyl group or a halogen atom such as chlorine, bromine or fluorine introduced into a cyclopentanone hydrophenanthrene ring to an extent that does not cause harmful effects on the purpose of the present invention, where this ring system may be saturated or partially unsaturated. Preferably, a residue of a sterol derivative is a group obtained by removing a hydrogen atom from a hydroxy group at position 3 in cholesterol, cholestanol or dihydroxycholesterol. More preferably, it is a group obtained by removing a hydrogen atom from a hydroxy group at position 3 in cholesterol. Sterol of a steroloxycarbonyl group may be derived from animal or plant oil resources, such as cholesterol, cholestanol, dihydrocholesterol, cholic acid, campesterol and cystosterol.

The above-mentioned cationic polymer may be produced as follows.

Poly(amino acid)s represented by Formulae (2)-(4) above may be produced, for example, by: introducing a polyamine residue into the side-chain of the poly(amino acid) through aminolysis of polyamino acid ester produced by polymerization of a known aspartate ester-derived N-carbonic anhydride by using a polyamine corresponding to the polyamine residue of the groups represented by $R^{23}$, $R^{33}$ and $R^{44}$; activating, if necessary, an amino group of the introduced polyamine moiety and a carboxyl group of carboxylic acid corresponding to an acyl group having the above-mentioned aliphatic hydrocarbon residue; and subsequently causing an appropriate amount of the activated carboxylic acid to react with the amino group.

4. Block Copolymer

According to the present invention, although the cationic polymer may be a polymer (homopolymer) consisting only of a polycation moiety as described above, it may be, without limitation, for example, a block copolymer or a graft polymer having a polyethylene glycol (PEG) moiety and a polycation moiety. An appropriate and preferable embodiment may be selected according to the application of the complex of the present invention.

The structures (e.g., polymerization degree, etc.) of PEG and a polycation are not limited and any structure may be selected, among which the polycation is preferably a polypeptide having a cationic group in the side-chain.

A polyplex of the present invention may be a core-shell micellar complex which is obtained by interaction between a nucleic acid and a part (a polycation moiety) of the block copolymer that gives a core moiety as an ion complex, and the rest part (a moiety containing the PEG moiety) of the block copolymer forms a shell moiety around the core moiety.

Examples of block copolymers include those represented by General Formula (5) below.

(wherein, $L^{2a}$ represents OCO, OCONH, NHCO, NHCOO, NHCONH, CONH or COO, $L^{3a}$ represents NH or CO, and q1 represents an integer of 1-6), m13, m14 and m15 independently represent an integer of 0-500 (provided that the sum of m13, m14 and m15 is an integer of 10-500), m16 represents an integer of 1-5, m17 represents an integer of 1-5, n represents an integer of 0-500, and the sign "/" indicates that the sequential order of the (m13+m14+m15) numbers of monomer units on both sides of the sign is arbitrary].

Here, in the cationic polymer of General Formula (5) above, —$R^{53}$ and/or —$R^{54}$ group represents a residue derived from an amine compound having a primary amine, and may be applied in the same manner as described for General Formula (2) above. For example, it may be a group represented by General Formula (22) or (23) above, and preferably a group represented by General Formula (23).

In the structure of General Formula (5), the block moiety accompanied by the repeating unit number (degree of polymerization) "n" is a PEG moiety, while the block moiety including the moieties accompanied by the repeating unit numbers "m13", "m14" and "m15" (in General Formula (5), moieties within the square brackets) are a polycation moiety. Moreover, the sign "/" in the structural formula of the polycation moiety indicates that the sequential order of the monomer units on both sides of the sign is arbitrary. For example, when a block moiety consisting of monomer units A, B and C is indicated as $[-(A)_a-/-(B)_b-/-(C)_c-]$, the sum number (a+b+c) of monomers including "a" number of As, "b" number of Bs and "c" number of Cs may be randomly linked in any order (provided that all of As, Bs and Cs are linearly linked).

Examples of the above-mentioned linear or branched alkyl group with a carbon number of 1-12 include a methyl group, an ethyl group, a n-propyl group, an isopropyl group, a n-butyl group, a sec-butyl group, a tert-butyl group, a n-pentyl group, a n-hexyl group, a decyl group and an undecyl group.

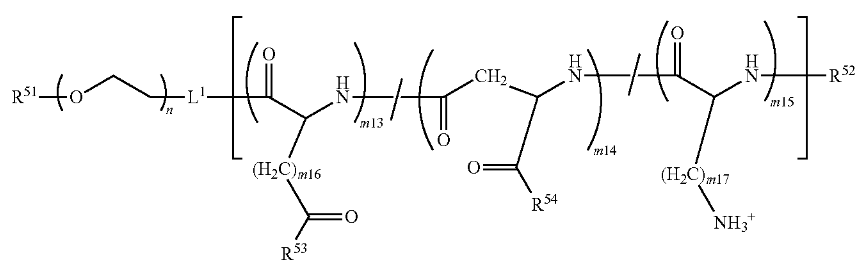
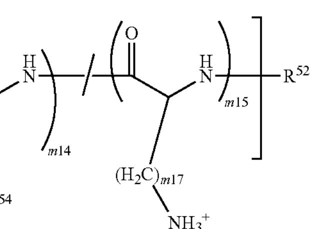

(5)

[wherein, $R^{51}$ and $R^{52}$ are synonymous with $R^{21}$ and $R^{22}$, respectively, and independently represent a hydrogen atom or an optionally substituted linear or branched alkyl group with a carbon number of 1-12, $R^{53}$ and $R^{54}$ are synonymous with $R^{23}$ and represent a residue derived from an amine compound having a primary amine, $L^1$ represents NH, CO, a group represented by General Formula (13) below:

$$—(CH_2)_{p1}—NH— \quad (13)$$

(wherein, p1 is an integer of 1-6), or a group represented by General Formula (14) below:

$$-L^{2a}-(CH_2)_{q1}-L^{3a}- \quad (14)$$

Examples of the above-mentioned substituent groups of the alkyl group include an acetalized formyl group, a cyano group, a formyl group, a carboxyl group, an amino group, an alkoxycarbonyl group with a carbon number of 1-6, an acylamide group with a carbon number of 2-7, a siloxy group, a silylamino group and a trialkylsiloxy group (alkylsiloxy groups independently have a carbon number of 1-6).

When the substituent group is an acetalized formyl group, it may be converted into another substituent group, i.e., formyl group (an aldehyde group; —CHO) by hydrolysis under mild acidic conditions.

In General Formula (5), $L^1$ as a linker moiety represents NH, CO, a group represented by General Formula (13) below:

$$—(CH_2)_{p1}—NH— \quad (13)$$

[wherein, p1 represents an integer of 1-6 (preferably 2-3)], or a group represented by General Formula (14) below:

$$-L^{2a}-(CH_2)_{q1}-L^{3a}- \quad (14)$$

[wherein, $L^{2a}$ represents OCO, OCONH, NHCO, NHCOO, NHCONH, CONH or COO, $L^{3a}$ represents NH or CO, and q1 represents an integer of 1-6 (preferably 2-3)].

In General Formula (5), n represents the number of the repeating unit (degree of polymerization) of the PEG moiety, which is specifically an integer of 0-500 (preferably 100-400, and more preferably 200-300).

Additionally, m13, m14 and m15 as degrees of polymerization of respective monomer units constituting the polycation moiety independently represent an integer of 0-500 (preferably 0-100, more preferably 10-100, still more preferably 20-100, and yet still more preferably 30-100) (provided that the sum of m13, m14 and m15 (m13+m14+m15) is 10-500 (preferably 10-300, more preferably 20-200, still preferably 30-150, still more preferably 40-120, yet still more preferably 50-100, and particularly preferably 60-70)).

A molecular weight (Mw) of the cationic polymer represented by General Formula (5) is preferably, but not limited to, 23,000-45,000, and more preferably 28,000-34,000. As to each block moiety, a molecular weight (Mw) of the PEG moiety is preferably 8,000-15,000, and more preferably 10,000-12,000 while a molecular weight (Mw) of the polycation moiety is preferably 15,000-30,000, and more preferably 18,000-22,000 in total.

A method for producing a cationic polymer represented by General Formula (5) may be, for example, but limited to, a method comprising: synthesizing a segment (a PEG segment) containing $R^{51}$ and a block moiety of a PEG chain in advance; sequentially polymerizing certain monomers on one end of this PEG segment (the end opposite to $R^{51}$); and, if necessary, thereafter substituting or converting the side-chain to contain a cationic group. Alternatively, another example may be a method comprising: synthesizing the PEG segment and a block moiety containing a side-chain having a cationic group; and linking them to each other. Methods and conditions for reactions employed in these production methods may appropriately be selected or determined considering a common procedure.

The above-mentioned PEG segment may be prepared, for example, by employing a method for producing a PEG segment moiety of a block copolymer described in publications WO 96/32434, WO 96/33233 and WO 97/06202. Among the PEG segments, the end opposite to the —$R^{51}$ group corresponds to "-$L^1$" moiety in General Formula (5), and it is preferably —$NH_2$, —COOH, a group represented by General Formula (6) below:

$$—(CH_2)_{p2}—NH_2 \quad (6)$$

[wherein, p2 represents an integer of 1-5 (preferably 2-3)], or a group represented by General Formula (7):

$$-L^{2b}-(CH_2)_{q2}-L^{3b} \quad (7)$$

[wherein, $L^{2b}$ represents OCO, OCONH, NHCO, NHCOO, NHCONH, CONH or COO, $L^{3b}$ represents $NH_2$ or COOH and q2 represents an integer of 1-6 (preferably 2-3)].

A specific method for producing a cationic polymer represented by General Formula (5) may comprise: synthesizing a block copolymer by polymerizing the amino terminal with N-carbonic anhydride (NCA) of a protected amino acid such as β-benzyl-L-aspartate (BLA) and Nϵ-Z-L-lysine by using a PEG segment derivative having the amino group at the terminal; and thereafter substituting or converting the side-chain of each block moiety with diethylenetriamine (DET) or the like to have the above-described cationic group. (For example, see publication WO 2007/99660, N. Kanayama et al., *ChemMedChem* 1 (4) 439-444 (2006) or the like).

5. Nucleic Acid

In one embodiment, a nucleic acid comprised as a constituent of a core moiety in a complex of the present invention is plasmid DNA or siRNA (small interfering RNA). siRNA is capable of suppressing the expression of a gene of interest through RNA interference (RNAi). Preferable examples of genes of interest include, but not limited to, a cancer (tumor) gene, an antiapoptotic gene, a cell cycle-related gene and a proliferation signal gene. Furthermore, the base length of siRNA is not limited but generally less than 30 bases (preferably 19-21 bases).

In this regard, according to the present invention, the nucleic acid comprised is not limited to plasmid DNA and siRNA only, and if necessary, other nucleic acids such as antisense Oligo DNA, decoy nucleic acid (double-stranded DNA), various RNAs, various suppressor genes (cancer suppressor gene, etc.), a chemically-modified nucleic acid or a non-native nucleic acid analog (for example, PNA (peptide nucleic acid)) may be comprised.

Since a nucleic acid molecule such as siRNA is a polyanion, it may bind to (associate with) the side-chain of the polycation moiety of the above-described block copolymer through electrostatic interaction.

6. Ternary Polyplex

A complex of the present invention is a complex of a polymer compound that can be obtained by forming a polyplex with a nucleic acid and a polycation and adding a charge conversional polymer, i.e., the above-mentioned anionic polymer (for example, pAsp (DET-Aco)), thereto. This complex is also referred to as a ternary polyplex (polyion complex:PIC).

A ternary polyplex of the present invention comprises a core moiety consisting of a nucleic acid and a polycation moiety bound via electrostatic interaction, and an anionic polymer (for example, pAsp(DET-Aco)) surrounding the core moiety.

A ternary polyplex of the present invention may readily be prepared, for example, by mixing a nucleic acid and a cationic polymer in any buffer (for example, Tris buffer) to form a polyplex and subsequently adding pAsp(DET-Aco) thereto.

The size of the PIC of the present invention is not limited but, for example, the particle size as measured by dynamic light scattering measurement (DLS) is preferably 5-200 nm, and more preferably 10-150 nm.

An example of the ternary polyplex of the present invention includes a conjugate in which a nucleic acid is bound to a polycation moiety in a block copolymer as the above-described cationic polymer via electrostatic interaction. Specifically, the above-described cationic polymer further contains a polyethylene glycol moiety such that the nucleic acid and the polycation moiety of the cationic polymer form a core moiety, and the polyethylene glycol moiety of the cationic polymer forms a shell moiety around the core moiety.

The ternary polyplex of the present invention may readily be prepared by mixing a nucleic acid (for example, plasmid DNA or siRNA) with a block copolymer in any buffer (for example, Tris buffer, etc.), but it should be prepared under sufficiently reductive conditions so as to avoid disulfide binding and resulting aggregation of only block copolymers prior to electrostatic binding between the block copolymer and the nucleic acid. For example, reductive conditions may be adjusted by adding DTT (dithiothreitol) or the like.

A mixture ratio of the block copolymer to the nucleic acid is not limited but, for example, the ratio (N/P ratio) of the total number (N) of cationic groups (for example, amino groups) in the block copolymer to the total number (P) of phosphate groups in the nucleic acid is preferably 0.5-100, more preferably 0.5-10, still more preferably 1-10, yet still more preferably 1-4, and particularly preferably 1-2. Similarly, the N/P ratio where the block copolymer is a copolymer represented by General Formula (5) is preferably 0.5-10, more preferably 0.5-4, and still more preferably 1-2. "N" in this case is the sum of primary and secondary amines contained in the side-chain of the polycation moiety.

An N/P ratio within the above range is preferable in that no free polymer is present and high in vivo expression efficiency can be obtained. The above-mentioned cationic group (N) refers to a group that is capable of forming an ion bond with the phosphate group in the nucleic acid through electrostatic interaction.

The size of the ternary polyplex of the present invention is not limited but, for example, the particle size as measured by dynamic light scattering measurement (DLS) is preferably 30-150 nm, and more preferably 50-100 nm.

Although the ternary polyplex of the present invention is negatively charged in a buffer under neutral environment (pH 7.0-7.4, preferably pH 7.4), it is converted to have positive charge in a buffer under acidic environment (pH 5.0-6.8, preferably pH 5.5). The extracellular pH is 7.4 and the ternary polyplex is stable in the presence of serum protein. However, once the polyplex is incorporated into a cell and localized in an endosome, pH is reduced to 5.5 and the compound represented by Formula (I) (preferably cis-aconitic acid amide or citraconic acid amide) is degraded, where a polycation (pAsp (DET), etc.) having a function of rendering an endosomal membrane weak is exposed on the polyplex surface. Through such an action, the charge conversional ternary polyplex exhibits low toxicity and high gene transfection efficiency even for a very sensitive cell such as HUVEC (human umbilical vein endothelial cell) or the like.

7. Nucleic Acid Delivery Device

The present invention provides a nucleic acid delivery device comprising the above-described ternary polyplex (often simply referred to as a "polyplex"). The delivery device of the present invention can easily render a nucleic acid stable, which has been difficult to be delivered to a target cell in a stable state. Furthermore, change in the pH inside and outside the cell is utilized as means for efficiently introducing the intended nucleic acid in the core moiety of the polyplex into a target cell either in vitro or in vivo.

For example, a solution containing a polyplex containing an intended plasmid or siRNA is administered to a test animal for intake into a target cell in the body. Later, the polyplex taken into the cell migrates from the endosome to the cytoplasm. In response to the change in pH in the cytoplasm, this binding is broken, as a result of which substitution between the contained nucleic acid and the polyanion present in the cell is promoted, where disassociation of the polyplex allows release of the intended nucleic acid into the cytoplasm.

The delivery device of the present invention may be applied to, but not limited to, various animals such as human, mouse, rat, rabbit, pig, dog and cat. In general, a method for administering to a test animal employs parenteral usage such as drip infusion, where conditions such as dosage, number of doses and duration of administration may appropriately be determined according to the type and the condition of the test animal.

The delivery device of the present invention may be used for a treatment (gene therapy) in which an intended nucleic acid is introduced into a cell responsible for any of various diseases. Thus, the present invention may also provide a pharmaceutical composition comprising the polyplex for treating various diseases, a gene therapeutic agent comprising the pharmaceutical composition as an active ingredient for various diseases, and a method (particularly, a gene therapeutic method) employing the above-described PIC for treating various diseases.

The method and conditions for administration are the same as described above. Examples of various diseases include cancers (for example, lung cancer, pancreas cancer, brain tumor, hepatic cancer, breast cancer, colon cancer, neuroblastoma and bladder cancer), circulatory diseases, locomotor disorders and central nervous system diseases.

The above-described pharmaceutical composition may be prepared according to a conventional method by appropriately selecting an excipient, a filler, a bulking agent, a binder, a wetting agent, a disintegrating agent, a lubricant, a surfactant, a dispersant, a buffer, a preservative, a solubilizing aid, an antiseptic, a flavoring agent, a soothing agent, a stabilizer, a tonicity agent and the like generally used for drug production. Furthermore, a form of the pharmaceutical composition employed is usually an intravenous injection (including drip) and provided, for example, in a unit dosage ampule or in multi-dosage vials.

8. Kit for Nucleic Acid Delivery

A kit for delivering a nucleic acid of the present invention is characterized by comprising the above-described anionic polymer or a polymer complex of the present invention. This kit may preferably be used for RNAi-based gene therapy in which siRNA is introduced into any target cell such as a cancer cell.

As to the kit of the present invention, the storage state of the polymer is not limited and any state such as a solution or powder form may be selected considering the stability (storage property) and convenience.

The kit of the present invention may comprise components other than the above-described anionic polymer and polymer complex. Examples of other components include a nucleic acid to be introduced into a cell, various buffers for dissolution, dilution or the like, a lysis buffer, various proteins and an instruction (user manual), which may appropriately selected according to the intended use and the type of the polymer used.

The kit of the present invention is used for preparing a polyion complex (PIC) having, as a core moiety, a nucleic acid of interest (for example, plasmid DNA or siRNA) to be introduced into a target cell. The prepared PIC may effectively be used as a device for delivering a nucleic acid into a target cell.

Hereinafter, the present invention will be described more specifically by means of examples. Examples of the invention, however, are not limited to the following examples.

Example 1

Materials and Methods

1. Materials

N,N-dimethylformamide (DMF) (Wako Pure Chemical Industries, Ltd, Japan), dichloromethane (DCM) (Wako, Japan), n-butylamine, ethylenediamine(1,2-diaminoethane), and diethylenetriamine(bis(2-aminoethyl)amine) (Tokyo Chemical Industry Co. Ltd, Japan) were purchased and redistilled before use. Acetic acid and hydrochloric acid were purchased and used without further purification (Wako, Japan). 1-methyl-2-pyrrolidinone (NMP), cis-aconitic anhydride, succinic anhydride and bovine serum albumin were purchased from Sigma (St. Louis, Mo.). β-benzyl-L-aspartate-N-carboxy-anhydride (BLA-NCA) was obtained from Nippon Oil and Fats Co., Ltd. (Tokyo, Japan).

2. Synthesis

2-1. Synthesis of PBLA (poly(β-benzyl-L-aspartate)) (2)

PBLA was prepared by ring-opening polymerization of BLA-NCA initiated by the terminal amino group of n-butylamine. n-butylamine (0.0417 mmol) was dissolved in 5 mL of DMF/DCM (1:10). BLA-NCA (4.60 mmol) solution in 8 mL of DMF/DCM (1:10) solution was added to an n-butylamine solution and the reaction mixture was stirred under an argon atmosphere at 35° C. for 48 hours. The obtained polymer was precipitated in diethyl ether (150 mL). The crude precipitate was washed twice with diethyl ether to obtain the final product as white powder. Based on $^{1}H$ NMR measurement, the degree of polymerization (DP) of BLA units was calculated to be 102. JEOL EX 300 spectrometer was used to record the entire NMR spectra at 300 MHz. Chemical shift downfield from tetramethylsilane is reported in ppm. $^{1}H$ NMR ($CDCl_3$): δ0.87 (3H, $CH_3CH_2CH_2CH_2NH$), δ1.27 (3H, $CH_3CH_2CH_2CH_2NH$), δ2.69, 3.12 (206H, $COCHCH_2COOCH_2Ph$, $CH_3CH_2CH_2CH_2NH$), δ4.28 (102H, COCHNH), δ5.07 (204H, $COOCH_2Ph$), δ7.27 (510H, $COOCH_2Ph$), δ8.88 (102H, COCHNH).

2-2. Syntheses of pAsp(EDA) (poly[(2-aminoethyl) aspartamide]) (3) and pAsp(DET) (poly(2-[(2-aminoethyl)amino]ethylaspartamide)) (4)

PBLA (0.802 mmol benzylester) was dissolved in NMP (10 mL). Diethylenetriamine (DET) (40.1 mmol) was added to the solution and the reaction mixture was stirred at 0° C. for an hour. The resulting solution was allowed to drip in 10% aqueous acetate solution (30 mL). The neutralized solution was dialyzed at 4° C. against 0.01M hydrochloric acid solution (×3) and distilled water (×3). Following lyophilization, pAsp(DET) was obtained as white powder of hydrochloride salt. According to $^{1}H$ NMR, no benzyl peak was confirmed. Synthesis of pAsp(EDA) was performed in the same manner except that ethylenediamine (EDA) was used instead of DET. $^{1}H$ NMR ($D_2O$): δ0.87 (3H, $CH_3CH_2CH_2CH_2NH$), δ1.27 (4H, $CH_3CH_2CH_2CH_2NH$), δ2.63 (408H, $COCHCH_2CONHCH_2CH_2NHCH_2CH_2NH_2$, $COCH_2CHCONHCH_2CH_2NHCH_2CH_2NH_2$, $COCHCH_2CONHCH_2CH_2NHCH_2CH_2NH_2$), δ2.76 (204H, $COCHCH_2CONHCH_2CH_2NHCH_2CH_2NH_2$), δ2.94 (204H, $COCHCH_2CONHCH_2CH_2NHCH_2CH_2NH_2$), δ3.20-3.50 (308H, $CH_3CH_2CH_2CH_2NH$, $COCHCH_2CONHCH_2CH_2NHCH_2CH_2NH_2$)

2-3. Syntheses of pAsp(EDA-Suc) (poly[(N'-succinyl-2-aminoethyl)aspartamide]) (5) and pAsp(DET-Aco) (poly(2-[([N'-cis-aconityl]-2-aminoethyl) amino]ethylaspartamide)) (6)

pAsp(DET) (0.055 mmol primary amine) was dissolved in 0.5 M $NaHCO_3$ buffer (pH 9.0, 50 mL). Cis-aconitic anhydride (2.76 mmol) (Aco) was added to the solution and stirred at 0° C. for 3 hours. The reaction mixture was purified using Amicon Ultra (MWCO=10,000; Millipore (Billerica, Mass.)) (using ×3 distilled water). Following lyophilization, the final product was obtained as white powder. According to calculation based on $^{1}H$ NMR, conversion yield exceeded 99%. Synthesis of pAsp(EDA-Suc) was performed in the same manner except that succinate anhydride (Suc) and pAsp (EDA) were used instead of Aco and pAsp(DET), respectively. $^{1}H$ NMR of PEG-pAsp(DET-cisAco) ($D_2O$): δ0.87 (3H, $CH_3CH_2CH_2CH_2NH$), δ01.27 (4H, $CH_3CH_2CH_2CH_2NH$), δ1.78 (204H, $COCHC(COONa)CH_2COONa$), δ2.67, δ2.76, δ2.94, δ3.20 (920H, $CH_3CH_2CH_2CH_2NH$, $COCHCH_2CONHCH_2CH_2NHCH_2CH_2NH_2$), δ5.43-5.71 (102H, $COCHC(COONa)CH_2COONa$).

Schemes: Synthetic schemes of pAsp(DET) (4), pAsp(EDA-Suc) (5) and PAsp(DET-Aco) (6)

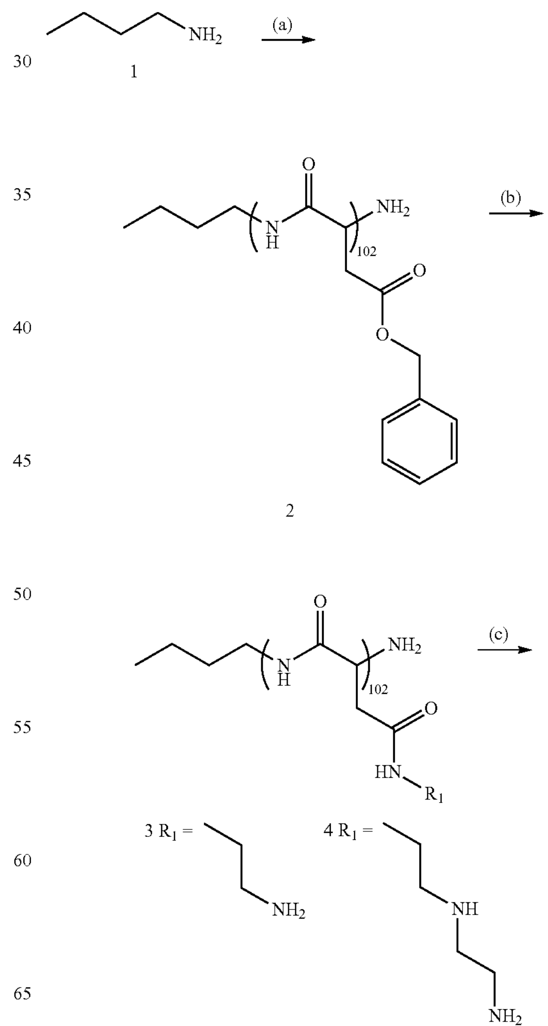

-continued

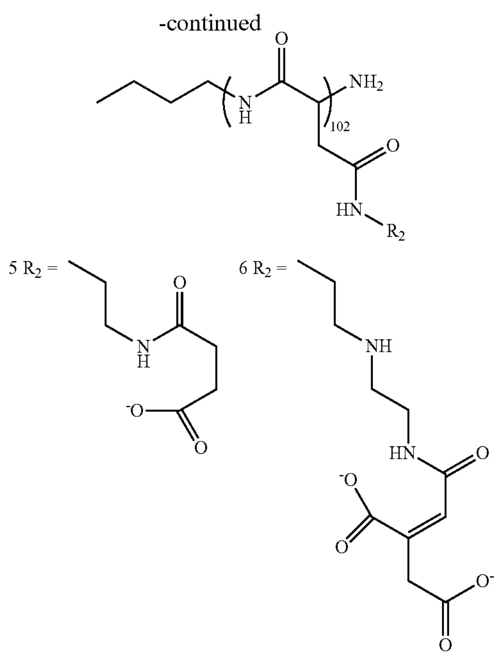

(a) BLA-NCA, DMF/DCM; (b) DET (or EDA), NMP;
(c) cis-aconitic anhydride (or succinate anhydride), pH 9.0 buffer 3. Preparation of Plasmid DNA CAG promoter and a plasmid coding for luciferase were supplied from RIKEN Bioresource Center (Japan) (H. Niwa et al. Gene, 1991, 108, 193-199). In addition, SEYFP-F46L (Venus) fragment (which is a mutant of yellow fluorescent protein, containing mutation of F46L (T. Nagai et al. Nat. Biotechnol., 2002, 20, 87-90)) was supplied from RIKEN. This fragment was inserted into pCAcc vector (pCAcc+Venus). This plasmid was amplified in competent DH5 *E. coli*, and purified using HiSpeed Plasmid MaxiKit (QIAGEN Science Co., Inc., Germany). The plasmid concentration was determined by absorbance at 260 nm.

4. Formation of Ternary Polyplexes pAsp(DET) (1 mg/mL) and plasmid DNA (50 μg/mL) were simply mixed at various N/P ratios (4-8) to obtain positive polyplexes. Here, the N/P ratios are defined as the excess molar ratios of amine units in pAsp(DET) to phosphate units in pDNA. After 15 minutes of incubation at room temperature, pAsp(DET-Aco) (or pAsp(EDA-Suc)) solution (1 mg/mL) was added to the positive polyplexes. The molar ratios between pAsp(DET) and pAsp(DET-Aco) (or pAsp (EDA-Suc)) fluctuated between 1-4. After incubation at room temperature for 15 minutes or longer, ternary polyplexes were obtained.

5. DLS Measurements of Polyplexes

See FIGS. 5 and 6

Each polyplex was diluted in an aqueous buffer (acetate buffer (pH 5.5, 10 mM) or Tris-HCl buffer (pH 7.4, 10 mM)). The final concentration of the plasmid DNA was 33 μg/mL. Each sample was incubated at 37° C., and then subjected to dynamic light scattering (DLS) measurement using Zetasizer Nano-ZS (green badge, ZEN3500, Malvern, Ltd. Malvern, U.K.) with He—Ne ion laser at 633 nm.

DLS distributions of DNA/pAsp(DET) positive polyplex (N/P ratio=6) and DNA/pAsp(DET)/pAsp(DET-Aco) ternary polyplex (N/P ratio=6) at pH 7.4 are shown in FIG. 5.

6. Zeta Potential Measurement

See FIG. 7

Zeta potentials of the positive polyplex and the ternary polyplex were determined based on laser Doppler electrophoresis (detection angle of 173°, temperature at 37° C.) using Zetasizer Nano-ZS (green badge, ZEN3500, Malvern, Ltd. Malvern, U.K.) with He—Ne ion laser at 633 nm. Each complex was diluted in an aqueous buffer (acetate buffer (pH 5.5, 10 mM) or Tris-HCl buffer (pH 7.4, 10 mM)). The final concentration of plasmid DNA was 33 μg/mL. Each sample was incubated at 37° C. Based on the resulting electrophoretic mobility, zeta potential of each complex was calculated from Smoluchowski equation: $\zeta=4\pi\eta\upsilon/e$ (where $\eta$ is the solvent viscosity, $\upsilon$ is the electrophoretic mobility and e is the solvent permittivity).

7. In Vitro Transfection

Human umbilical vein endothelial cells (HUVEC) were seeded into a collagen-coated 24-well culture plate and incubated in 400 μL of EBM™-2 containing insulin, hEGF, GA-1000, hFGF-B and FBS (5%), overnight. 40 μL of each sample solution was added to a medium (1 μg plasmid DNA/well). After 24 hours of incubation, the medium was exchanged for a fresh sample-free medium, and further incubated for 24 hours. The cells were washed with 400 μL of Dulbeccco's PBS and lysed with 100 μL of cell culture Promega lysis buffer. The luciferase activities of the lysates were evaluated from the luminescence intensities with Mithras LB 940 (Berthold Technologies). The resulting luciferase was normalized according to the protein amount in the lysate determined with Micro BCA™ protein assay reagent kit (Pierce). Venus (YFP) expression was observed using Biozeero BZ-8000 (Keyence) at excitation wavelength of 450-490 nm (emission filter: 510-560 nm).

8. Cell Viability Assay

See FIGS. 8 and 9

For cytotoxicity assay, HUVEC was incubated with the sample for 24 hours, and viability was evaluated by MTT assay (Cell Counting Kit-9, Dojindo, Kumamoto, Japan). According to the protocol provided by the manufacturer, absorbance was read at 450 nm to measure each well. At the same time, the results were indicated as relative value (%) to the value of a control cell that has been incubated with Tris-HCl buffer (10 mM, pH 7.4) only.

9. Stability of Complex in Albumin Solution

Each sample was diluted with bovine serum albumin (BSA) solution (in Tris-HCl buffer (10 mM, pH 7.4)). The final plasmid concentration was 33 μg/mL while the final BSA concentration was 2 mg/mL. After incubation at 37° C., the sizes of the complexes were measured by DLS as described above.

10. Observation with Confocal Laser Microscope (CLSM)

See FIG. 4

Using Label IT nucleic acid labeling kit (Mirus, Madison, Wis.), pDNA was labeled with Cy5. HUVEC (30,000 cells) were seeded into a 35 mm glass base dish (Iwaki, Japan) and incubated in 1 mL of EBM™-2 containing insulin, hEGF, GA-1000, hFGF-B and FBS (5%), overnight. After exchanging the medium for a fresh medium, 120 μL of the solution of the polyplex or ternary complex containing 3 μg of Cy5-labeled pDNA (N/P=6; pAsp(DET-Aco) (or pAsp(EDA-Suc)/pAsp(DET) molar ratio=2) was applied to the glass dish. After incubation, the medium was removed and the cells were washed twice with PBS. Intracellular distribution was observed with CLSM, and then the acidic late endosome and lysosome were stained with LysoTracker Green (Molecular Probes, Eugene, Oreg.) while the nucleus was stained with Hoechst 33342 (Dojindo Laboratories, Japan). LSM 510 (Carl Zeiss, Germany) was used (with 63× object lens (C-Apochromat, Carl Zeiss, Germany)) for CLSM observation for LysoTraker, Cy5 and Hoechst 33342 at excitation wavelengths of 488 nm (Ar laser), 633 nm (He—Ne laser) and 710 nm (Mai Tai laser), respectively.

Results

A polyplex of plasmid DNA and polycation was prepared. As the polycation, the present inventors selected poly{N—[N'-(2-aminoethyl)-2-aminoethyl]aspartamide} (pAsp (DET)) (see FIG. 2A). The group of the present inventors proved that this is a moiety that disrupts endosome with lower cytotoxicity as compared to conventional polycation (including PEI) and that renders the membrane instable[9]. Since the amount of the polycation is excessive (N/P ratio=4-8), the polyplex showed positive surface charge with approximately +40 mV zeta potential. Next, 1-4 equal molar amount of charge conversional polymer, i.e., poly(N-{N'-[(N"-cis-aconityl)-2-aminoethyl]-2-aminoethyl}aspartamide) (pAsp (DET-Aco)) (see FIG. 2A), was added to the polyplex to form a ternary polyplex. Note that pAsp(DET-Aco) is altered to pAsp(DET)a that can efficiently disrupt the endosome at pH after degradation of cis-aconitic acid amide. Each ternary polyplex showed unimodal size distribution at various charge ratios and had an average diameter of about 130 nm according to dynamic light scattering (DLS) measurement even in the presence of excessive pAsp(DET-Aco). Although there was a possibility that a binary polyplex of DNA-free pAsp(DET-Aco) and pAsp(DET) was formed, formation of a ternary polyplex containing DNA was confirmed by gel electrophoresis assay (see "Materials and methods" and FIGS. 5 and 6).

Figure 1:
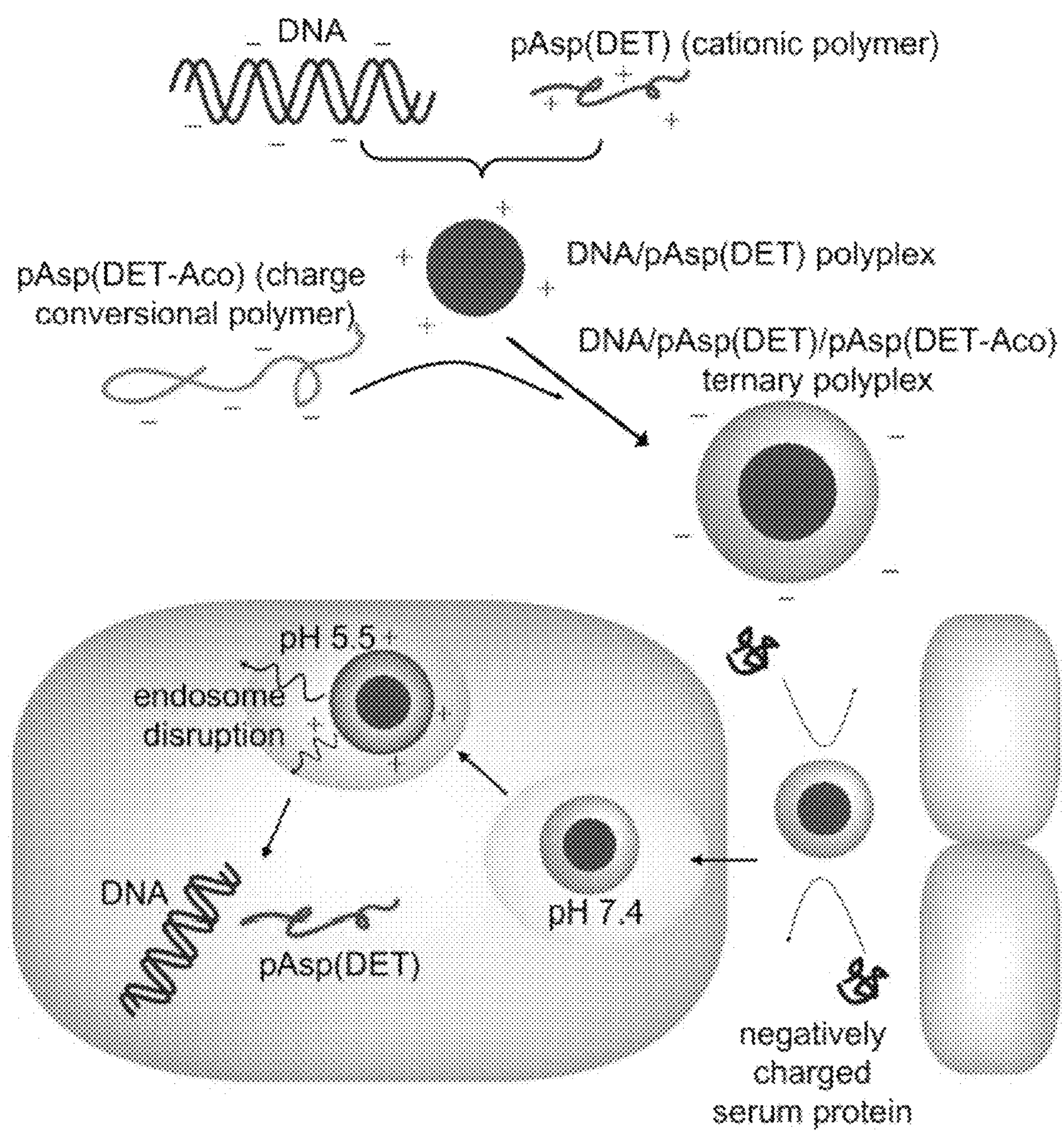
FIG. 1 is a schematic view of a charge conversional ternary polyplex having an endosome-disrupting function.
Figure 2:
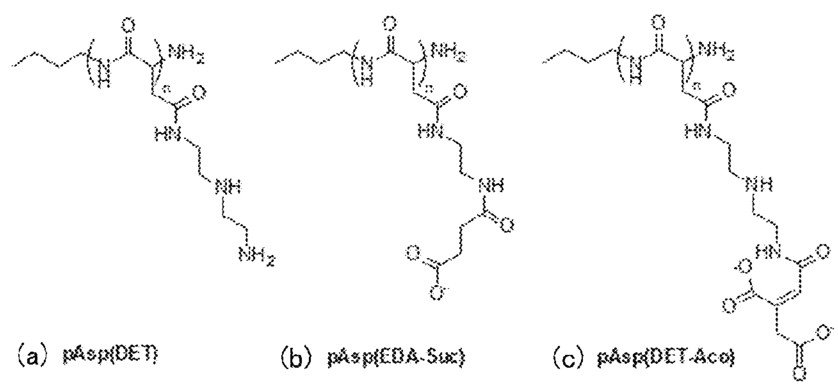
FIG. 2 shows structural formulae and charge conversion of polymers used in the present invention.
Figure 2:
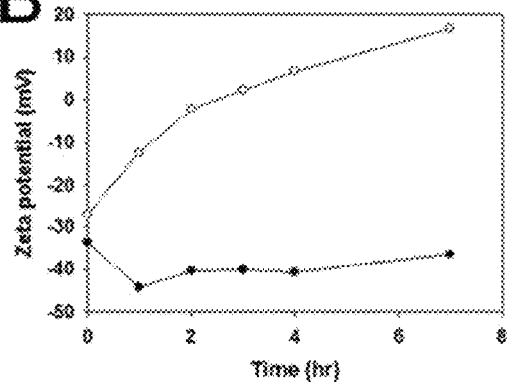
Figure 2:
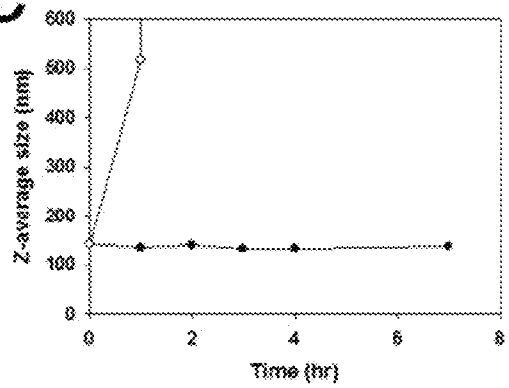

The charge conversional behavior of the ternary polyplex was monitored from the change in the zeta potential shown in FIG. 2B. The ternary polyplex maintained a zeta potential of around −40 mV at pH7.4. The zeta potential at pH 5.5, however, gradually changed from negative to positive, demonstrating charge conversion resulting from degradation of the cis-aconitic acid amide moiety. After incubation at pH 5.5 for 2 hours, the zeta potential reached 0 mV. As a negative control, the present inventors used a non-charge-conversional polycation having a similar structure, i.e., poly[(N'-succinyl-2-aminoethyl)aspartamide] (pAsp(EDA-Suc)) (see FIG. 2A). A ternary polyplex of pAsp(DET) and pAsp(EDA-Suc) maintained a zeta potential of around −40 mV at pH 5.5 and pH 7.4, with no sign of charge conversion (see "Materials and Methods" and FIG. 7).

This charge conversion also induced dramatic change in the size of the ternary polyplex. As shown in FIG. 2C, the ternary polyplex maintained a diameter of around 130 nm at pH 7.4, but the size promptly increased after an hour at pH 5.5. After 2 hours, large aggregates with diameters exceeding 1 μm were formed. This aggregation was caused possibly due to decrease in the repulsion force resulting from partial charge neutralization after an hour and complete neutralization after 2 hours (pH 5.5) as indicated by the data of the zeta potential measurement.

With respect to the possibility of in vivo application, one must focus on the stability of the polyplex in a serum protein solution. While the ternary polyplex retains the original diameter in a bovine serum albumin (BSA) solution, the diameter of the positive polyplex of pAsp(DET) promptly increased even after an hour of incubation (see FIG. 3A). Improvement of the stability of the ternary polyplex probably resulted from the repulsion force between the anionic ternary polyplex and BSA, which may be beneficial in the future systemic application.

Transfection was carried out using human umbilical vein endothelial cell (HUVEC). Only limited transfection reagents can be used since transfection of HUVEC is very difficult and HUVEC is highly sensitive to toxicity[10].

Transfection data obtained with luciferase pDNA was summarized in FIG. 3B. In both primary polyplex and ternary polyplex, N/P ratio of DNA and pAsp(DET) was 6, at which these polyplexes showed the highest transfection efficiency. Two molar equivalents of pAsp(DET-Aco) and pAsp(EDA-Suc) were added to form ternary polyplexes. The ternary polyplex of pAsp(EDA-Suc) as a control showed similar transfection efficiency as that of the primary polyplex of pAsp(DET), the charge conversional ternary polyplex of pAsp(DET-Aco) showed transfection efficiency that was more than ten times the transfection efficiency of ExGen 500 (linear PEI of a commercially available transfection reagent) and twice as high as the transfection efficiency of the pAsp (DET) polyplex. Although the negative surface charge of the ternary complex is useless for cellular uptake or endosomal escape, it is capable of increasing the stability and reducing the toxicity of the complex in the presence of the serum protein as shown in FIG. 3A. Hence, a non-charge-conversional ternary polyplex (DNA/pAsp(DET)/pAsp(DET-Suc)) was also capable of showing similar transfection efficiency. When the charge conversional endosome disruption moiety was introduced into the ternary polyplex (DNA/pAsp(DET)/pAsp(DET-Aco)) in favor of stability and low toxicity, transfection efficiency was further increased. The results of transfection using yellow fluorescent protein (YFP) pDNA are summarized in "Materials and Methods" described below (see FIGS. 8 and 9), which also show appropriate transfection efficiency of the ternary polyplex system.

Cytotoxicity measured by MTT assay is shown in FIG. 3C. At N/P ratios of 6 and 8 (which are optimal transfection ratios), ExGen 500 showed very high toxicity with viability of less than 10%. The viability of pAsp(DET) polyplex also decreased to 50%. One of the main reasons of the decreased viability was probably the membrane toxicity induced by the positive surface charge of the polyplext[11]. The ternary polyplexes that have negatively-charged surface outside the cell, however, showed almost no cytotoxicity at both N/P ratios.

In order to confirm the enhanced endosomal escape of the charge conversional ternary polyplex, Cy5-labeled pDNA was used to examine the intracellular distribution of the polyplex with a confocal laser microscope (CLSM) (see FIG. 4). Upon release of the polyplex from acidic organelle, the yellow fluorescence changes to red. The positively-charged pAsp(DET) polyplex showed significant endosomal escape even after 3 hours, and over 80% of DNA escape was observed after 24 hours. After 3 hours, both ternary polyplexes showed low endosomal escape. After 24 hours, however, the charge conversional ternary polyplex of pAsp(DET-Aco) showed endosomal escape that was more similar to that of the positive pAsp(DET) polyplex. Meanwhile, most part (more than 40%) of the non-charge-conversional polyplex of pAsp(EDA-Suc) remained in the endosome.

Quantitative analyses of CLSM images are summarized in FIG. 3D. The charge conversional polyplex showed similar behavior to that of the non-charge-conversional polyplex for up to 3 hours, but the degree of colocalization was lower after 7 hours and eventually the ratio was similar to that of the positive pAsp(DET) polyplex after 24 hours. Considering endosome acidification and later-required charge conversion, CLSM data seem to be rational and coincide with the luciferase transfection data.

In summary, the present inventors developed a ternary polyplex that was negatively charged at pH outside a cell and the charge changes to positive at pH in an endosome, where the endosome is disrupted. Eventually, the present inventors realized fairly high transfection activity and low toxicity effect on highly sensitive primary cells (HUVEC). The transfection efficiency of this ternary polyplex system may be further enhanced via conjugation with an appropriate ligand (for example, an RGD peptide for activating internalization through binding to integrin receptor)[12]. The concept of a charge conversional ternary polyplex having an endosome disruption moiety according to the present inventors can readily be applied to various highly sensitive primary cells. The efficient and chemical toxicity-free transfection according to this concept is one of the most important and urgent issues in the biomedical field. In addition, stability of the ternary polyplex in the presence of a negatively-charged serum protein is also advantageous for development of an in vivo gene vector.

Example 2

Experimental Method

1. Synthesis of Poly(L-Lysine) (PLL) Homopolymer

An eggplant shaped flask provided with a three-way stopcock was vacuum-dried, added with Lys(TFA)-NCA (1.01 g, 3.77 mmol) under an argon (Ar) atmosphere, and then added with DMSO (8 mL) for lysis. As an initiator, n-butylamine (5.4 mg, 73.8 μmol) was added to the monomer solution, and agitated for about 48 hours in a thermostatic bath at 35° C. After the reaction, the polymerization solution was slowly dripped in an excessive amount of thoroughly agitated diethyl ether to precipitate the polymer. Once most polymer has precipitated after about an hour of agitation, supernatant solution was removed by decantation. The precipitated polymer was dried under reduced pressure at room temperature. According to $^1$H NMR analysis, the chain length (degree of polymerization (DP) of lysine) was 52.

50 mg of P[lys(TFA)] (DP: 52) was dissolved in 5 ml of MeOH, added with 0.5 ml of 1N NaOH and agitated at 35° C. for 6 hours. After the reaction, dialyses against HCl solution with weak acidity and pure solution were conducted for three times each using dialysis membranes (Spectrum, MW Cut-Off: 6000-8000), and lyophilization was performed to collect polymers.

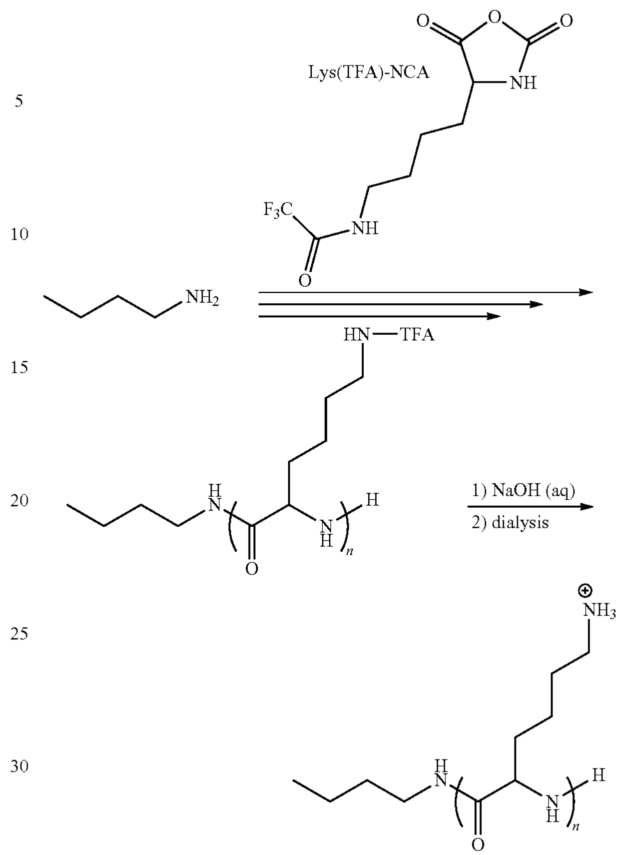

2. Syntheses of PAsp(DET(x)) (x=aco and suc)

PAsp(DET(x)) (x=aco and suc) were synthesized in the same manner as described in Example 1. A cationic polymer PAsp(DET) with a chain length (the number of asparagine units) of 133 was used.

3. Methods for Preparing pDNA/PLL Polyplex and Ternary Polyplex (i) pDNA/PLL Cationic Polyplex pDNA (CAG-Luc) dissolved in HEPES buffer (10 mM, pH 7.4) was mixed with PLL (DP=52) at N/P=2, and left to stand at 4° C. overnight to prepare pDNA/PLL polyplex (2/3 OD).

(ii) Ternary Polyplex

To the above-described cationic polyplex pDNA/PLL solution, a predetermined amount of PAsp(DET(aco)) or PAsp(EDA(suc)) was added and left to stand at 4° C. for 3 hours to prepare a ternary polyplex.

4. Measurements of Particle Sizes and Zeta Potentials of Ternary Polyplexes

Particle size and zeta potential measurements of the ternary polyplexes were carried out in the same manner as described in Example 1.

5. Transfection (Huh-7 and HUVEC)

20,000 cells per well were seeded into a 24-well dish, cultured for 24 hours and added with 31 μl of polyplex (pDNA concentration: 2/3 OD). The cell and the polyplex were brought into contact with each other for 24 hours. Then, the medium (DMEM) was exchanged for another 24 hours of cultivation. The gene expression activity was assessed by luciferase assay.

As cultured cells, human hepatic cancer cell (Huh-7) and normal human umbilical vein endothelial cell (HUVEC) were used.

6. Assessment of Uptake with Flow Cytometer 40,000 cells (Huh-7) per well were seeded into a 6-well dish, cultured for 24 hours and added with 60 μl of polyplex prepared with fluorescent dye (Cy5)-labeled pDNA (pDNA concentration: 2/3 OD). The cell and the polyplex were brought into contact with each other for 24 hours, washed with PBS 2-3 times, and treated with trypsin. Measurement was carried out by using BD LSR II analyzer from BD Biosciences.

7. Observation with Confocal Laser Microscope

Cells (Huh-7) were seeded into 35 mm petri dishes at 50,000 cells/well, cultured for 24 hours and added with 90 μl of polyplex prepared with fluorescent dye (Cy5)-labeled pDNA (pDNA concentration: 2/3 OD). The cells were brought into contact with the polyplex for 24 hours, and then the nuclei and the endosomes were stained with 5 μM of Lysto Tracker (20 μL) and Hoechst (10 μL). Just before the measurement, washing was performed with PBS for three times and 2 ml of medium was added for observation. LSM-510 from Carl Zeiss was used as the confocal laser microscope.

Experimental Results

1. Synthesis of Poly(L-Lysine) (PLL) Homopolymer

According to $^1$H NMR analysis, the chain length of polymer P[Lys(TFA)] (degree of polymerization (DP) of lysine) prior to deprotection was 52. Moreover, as a result of analysis by gel permeation chromatography (GPC), the polymer was free of oligomer or the like and highly monodispersed (FIG. 10).

Deprotected polymer samples were also similarly subjected to analyses by $^1$H NMR and GPC.

As a result, removal of the protecting group from P[Lys (TFA)] side-chain with TFA was confirmed, and hydrolysis of the main chain was not confirmed from analysis with aqueous GPC. The recovery rate of the polymer was 77%.

2. Syntheses of PAsp[DET(aco)] and PAsp[EDA(suc)]

PAsp[DET(aco)] and PAsp[EDA(suc)] were synthesized in the same manner as described in Example 1.

3. Physicochemical Assessments (Particle Size and Zeta Potential Measurements) of pDNA/PLL Polyplex and Ternary Polyplex To cationic polyplex pDNA/PLL, PAsp[DET(aco)] or PAsp[EDA(suc)] was added in an attempt to form a ternary polyplex. Results from the zeta potential measurements suggested that a negative surface charge was obtained when an equivalent, 2-, 3-, 4- and 5-fold mol of PAsp(DET(x)) was sequentially added to pDNA (FIG. 11). Furthermore, according to light scattering measurement, formation of polyplexes with particle sizes of about 110-130 nm was confirmed regardless of the amount of PAsp(DET(x)) added. According to these results, an anionic ternary polyplex with a stable particle size appeared to have formed without secondary aggregation or the like.

4. Transfection (Huh-7 and HUVEC)

The gene expression activity of PAsp(EDA(suc))-added ternary polyplex was equivalent to or lower than that of non-added cationic pDNA/PLL. On the other hand, the gene expression activity of PAsp[DET(aco)]-added ternary polyplex increased as compared to that of pDNA/PLL by about 20 and 10 times for Huh-7 and HUVEC, respectively (FIG. 12). Since PAsp[DET(aco)] polymer has a charge conversion function where its charge inverts in response to pH, this property seems to contribute to the increase in the expression activity.

5. Assessment of Uptake with Flow Cytometer pDNA/PLL only as a cationic polyplex, and two ternary polyplexes obtained by adding PAsp[DET(aco)] or PAsp [EDA(suc)] to this pDNA/PLL were evaluated for their intracellular uptakes. Results from flow cytometer analyses showed almost the same levels of uptakes for all polyplexes (FIG. 13).

For the PAsp[DET(aco)]-added polyplex, slight increase in the uptake was observed but this increase does not explain the 20-fold increase in the gene expression activity. In fact, difference in the intracellular dynamic behavior among the polyplexes seems to reflect the increase in the gene expression activities.

6. Observation with Confocal Laser Microscope pDNA/PLL only as a cationic polyplex, and two ternary polyplexes obtained by adding PAsp[DET(aco)] or PAsp [EDA(suc)] to this pDNA/PLL were observed with respect to intracellular dynamics with a confocal laser microscope. Many yellow regions were observed for the cationic polyplex pDNA/PLL and the ternary polyplex added with PAsp[EDA (suc)] (FIG. 14). This reflects that the polyplexes were trapped in the endosome. On the other hand, many red regions were distributed for the PAsp[DET(aco)]-added ternary polyplex. This strongly suggests that the polyplex had escaped from the endosome and transferred into the cytoplasm (FIG. 14).

Yet additionally, the polyplexes trapped in the endosomes were quantitatively evaluated based on these confocal laser microscope images. 70% or more of the cationic polyplex pDNA/PLL and the ternary polyplex added with PAsp[EDA (suc)] remained trapped in the endosome (FIG. 15). A polyplex using PLL homopolymer and a derivative thereof has very poor property of escaping from the endosome. Moreover, since PAsp[EDA(suc)] does not have a function of inverting the charge in response to acidic pH, even when it is made into a ternary polyplex, improvement of the intracellular dynamics, that is, enhancement of the efficiency of escaping from the endosome, was not realized. On the other hand, the PAsp[DET(aco)]-added ternary polyplex that remained trapped was about 40% (FIG. 15). This indicates that the polyplex had efficiently escaped from the endosome, and this behavior seems to have contributed to the significant increase in the gene expression activity.

Example 3

Experimental Method

1. Synthesis of N-Succinimidyl Octadecanoate

N-succinimidyl octadecanoate was synthesized according to a known method [N. M. Howarth, W. E. Lindsell, E. Murray, P. N. Preson, Tetrahedron 61 (2005) 8875-8887]. Stearic acid (1.87 g, 6.56 mmol) and N-hydroxysuccinimide (0.76 g, 6.56 mmol) was dissolved in 80 mL of dichloromethane (DCM), and allowed to react with 1-ethyl-3-(3-dimethylaminopropyl)-carbodiimide hydrochloride (WSC) (1.25 g, 6.56 mmol) for 48 hours. Thereafter, the resultant was washed with water, extracted twice with DCM and dried with $MgSO_2$ to obtain white powder (amount 1.4 g, yield 56%). The conversion ratio of the carboxyl group of stearic acid was 96% as calculated by $^1$H-NMR.

2. Synthesis of Stearoyl Group-Introduced Poly(L-Lysine)

poly(L-Lysine) (molecular weight 20,000) and DIPEA were dissolved in methanol, and allowed to react with N-succinimidyl octadecanoate dissolved in a small amount of dichloromethane at 4° C. for 24 hours. At the end of the reaction, the resultant was reprecipitated with diethylether. The filtrated sample was dissolved in methanol/water (1:1 v/v) and dialyzed three times against 0.01M aqueous HCl solution and once against distilled water at 4° C. Subsequently, the resultant was collected by lyophilization, thereby synthesizing poly(L-Lysine) introduced with stearoyl groups into the side-chain for 15%, 28% and 45% (PLL-ST).

3. Preparation of siRNA-Bearing Ternary Polyplex, and Assessment and MTT Assay for Gene Knockdown Efficiency siRNA/PLL-ST ternary polyplex was obtained by mixing siRNA dissolved in HEPES buffer (10 mM, pH 7.4) with PLL-ST such that the ratio of the phosphate residue of siRNA to the lysine residue was 1.4, then mixing the resultant with PAsp(DET(aco)) at different mixture ratios, and left to stand at 4° C. for 3 hours.

In siRNA inhibitory assay, Huh-7 cell was seeded at 40,000 cells/well, transfected with plasmids that express GL3 luciferase and Rellina luciferase using Lipofectamine 2000, added with GL3 luciferase siRNA-bearing ternary polyplex (siRNA concentration: 100 nM) and cultured for 48 hours. The inhibitory effect of siRNA on the expression of GL3 luciferase was evaluated by calculating the ratio of luciferase luminescence (GL3/Rellina) after the addition of GL3 and Rellina substrates.

On the other hand, in MTT assay, Huh-7 cell was seeded at 10,000 cells/well, added with GL3 luciferase siRNA-bearing ternary polyplex (siRNA concentration: 100 nM) and cultured for 48 hours. Thereafter, viability of the cell was evaluated by MTT assay.

Experimental Results

1. Assessment of Gene Knockdown Efficiency of siRNA-Bearing Ternary Polyplex

The gene knockdown efficiency of the siRNA-bearing ternary polyplex was enhanced with the increase in the efficiency of stearoyl group introduction. It was confirmed that, when PAsp(DET(aco)) was added, the gene knockdown efficiency was enhanced at mixture ratios of 0.7 and 1.4 whereas the gene knockdown efficiency decreased at mixture ratios of 2.8 and 5.6 (FIG. 16(A)). While exposure of PAsp(DET) seemed to have promoted endosomal escape of the polyplex when the mixture ratios of PAsp(DET(aco)) were 0.7 and 1.4, the intracellular uptake of the polyplex seemed to decrease as the surface of the polyplex became anionic at the mixture ratios of 2.8 and 5.6. The results shown in FIG. 16(A) seemed to have resulted for these reasons.

2. Cytotoxicity Assessment of siRNA-Bearing Ternary Polyplex

Increase in cytotoxicity of a siRNA-bearing ternary polyplex was observed for ternary polyplexes whose stearoyl group introduction rates of PLL-ST were 28% and 45% and whose mixture ratios to PAsp(DET(aco)) were 0.7 and 1.4. Meanwhile, cytotoxicities were found to decrease for a ternary polyplex whose stearoyl group introduction rate of PLL-ST was 15% and for ternary polyplexes whose stearoyl group introduction rates of PLL-ST were 28% and 45% and whose mixture ratios to PAsp(DET(aco)) were 2.8 and 5.6 (FIG. 16(B)). These results show that excessive introduction of the stearoyl groups to PLL may increase the cytotoxicity thereof, but it can be reduced by addition of PAsp(DET(aco)).

Thus, preparation of a ternary polyplex associated with the addition of PAsp(DET(aco)) seems to reduce the cytotoxicity while maintaining the siRNA transfection activity of the polycation constituting the nucleus.

REFERENCES

[1] a) D. W. Pack, A. S. Hoffman, S. Pun, P. S. Stayton, Nat. Rev. Drug Discovery 2005, 4, 581-593; b) E. Mastrobattista, M. A. E. M. Aa, W. E. Hennink, D. J. A. Crommelin, Nat. Rev. Drug Discovery 2006, 5, 115-121.

[2] a) O. Boussif, F. Lezoualc'h, M. A. Zanta, M. D. Mergny, D. Scherman, B. Demeneix, J. P. Behr, Proc. Natl. Acad. Sci. U.S.A. 1995, 92, 7297-7301; b) M. Neu, D. Fischer, T. Kissel, J. Gene Med. 2005, 7, 992-1009.

[3] a) M. X. Tang, C. T. Redemann, F. C. Szoka, Bioconjugate Chem. 1996, 7, 703-714; b) R. Wattiaux, N. Laurent, S. W-D. Coninck, M. Jadot, Adv, Drug Del. Rev. 2000, 41, 201-208.

[4] a) A. C. Hunter, Adv. Drug Deliv. Rev. 2006, 58, 1523-1531; b) M. Ogris, S. Brunner, S. Schiller, R. Kircheis, E. Wagner, Gene Ther. 1999, 6, 595-605.

[5] V. S. Trubetskoy, S. C. Wong, V. Subbotin, V. G. Budker, A. Loomis, J. E. Hagstrom, J. A. Wolff, Gene Ther. 2003, 10, 261-271.

[6] M. Han, Y. Bae, N. Nishiyama, K. Miyata, M. Oba, K. Kataoka, J. Controlled Rel. 2007, 121, 38-48.

[7] a) E. R. Gillies, A. P. Goodwin, J. M. Fréchet, Bioconjugate Chem. 2004, 15, 1254-1263; b) M. Kramer, J. F. Stumbé, H. Turk, S. Krause, A. Komp, L. Delineau, S. Prokhorova, H. Krautz, R. Haag, Angew. Chem. Int. Ed. 2002, 41, 4252-4246.

[8] a) Y. Lee, S. Fukushima, Y. Bae, S. Hiki, T. Ishii, K. Kataoka, J. Am. Chem. Soc. 2007, 129, 5362-5363; b) D. B. Rozema, D. L. Lewis, D. H. Wakefield, S. C. Wong, J. J. Klein, P. L. Roesch, S. L. Bertin, T. W. Reppen, Q. Chu, A. V. Blokhin, J. E. Hagstrom, J. A. Wolff, Proc. Natl. Acad. Sci. U.S.A. 2007, 104, 12982-12987.

[9] a) N. Kanayama, S. Fukushima, N. Nishiyama, K. Itaka, W-D. Jang, K. Miyata, Y. Yamasaki, U-I. Chung, K. Kataoka, Chem. Med. Chem. 2006, 1, 439-444; b) K.

Masago, K. Itaka, N. Nishiyama, U. Chung, U., K. Kataoka, Biomaterials 2007, 28, 5169-5175.

[10] a) V. Zaric, D. Weltin, P. Erbacher, J. S. Remy, J. P. Behr, D. Stephan, J. Gene Med. 2004, 6, 176-184; b) J. J. Green, G. T. Zugates, N. C. Tedford, Y. H. Huang, L. G. Griffith, D. A. Lauffenburger, J. A. Sawicki, R. Langer, D. G. Anderson, Adv. Mater. 2007, 19, 2836-2842.

[11] a) D. Fischer, Y. Li, B. Ahlemeyer, J. Krieglstein, T. Kissel, Biomaterials 2003, 24, 1121-1131; b) S. M. Moghimi, P. Symonds, J. C. Murray, A. C. Hunter, G. Debska, A. Szewczyk, Mol. Ther. 2005, 11, 990-995.

[12] a) K. Temming, R. M. Schiffelers, G. Molema, R. J. Kok, Drug Resist Updat. 2005, 8, 381-402; b) M. Oba, S. Fukushima, N. Kanayama, K. Aoyagi, N. Nishiyama, H. Koyama, K. Kataoka, Bioconjugate Chem. 2007, 18, 1415-1423.

INDUSTRIAL APPLICABILITY

The present invention provides a charge conversional ternary polyplex. The polyplex of the present invention is capable of delivering a nucleic acid to a cell with high efficiency without raising toxicity, and thus is extremely useful for gene therapy and the like.

The invention claimed is:

1. A polymer complex comprising a nucleic acid, a cationic polymer and an anionic polymer of Formula (1):

(1)

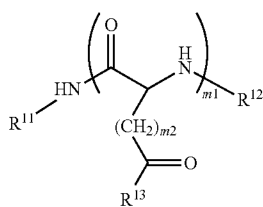

wherein $R^{11}$ represents $CH_2CH_2CH_2CH_3$, $R^{12}$ represents hydrogen atom, $R^{13}$ represents a conjugate of a residue derived from an amine compound having a primary amine, and a compound selected from the group consisting of Formula (Ia)-(Ig) below:

(Ia)

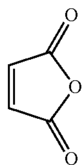

(Ib)

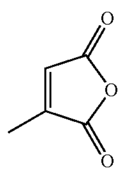

(Ic)

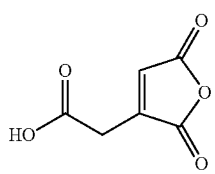

-continued (Id)

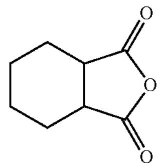

(Ie)

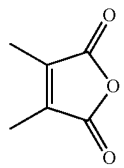

(If)

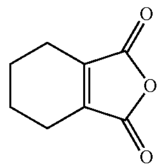

(Ig)

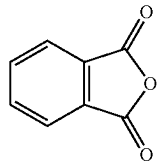

m1 represents an integer of 10-500, and m2 represents an integer of 1-5;

wherein the residue derived from an amine compound having a primary amine is a group of Formula (11):

$$—NH—(CH_2)_r—X^{11} \quad (11)$$

wherein $X^{11}$ represents $—NH_2$ or $—NH_3^+$, and r represents an integer of 0-5, or a group of Formula (12):

$$—[NH—(CH_2)_{s1}]_{t1}—X^{12} \quad (12)$$

wherein $X^{12}$ represents $—NH_2$ or $—NH_3^+$, and s1 and t1, independently from each other and independently between the $[NH—(CH_2)_{s1}]$ units, represent integers of 1-5 and 2-5, respectively.

2. The polymer complex according to claim 1, wherein the residue derived from an amine compound having a primary amine is $—NH—NH_2$ or $—NH—(CH_2)_2—NH—(CH_2)_2—NH_2$.

3. The polymer complex according to claim 1, wherein the compound selected from the group consisting of Formula (Ia)-(Ig) is Formula (Ib) or (Ic) below:

(Ib)

(Ic)

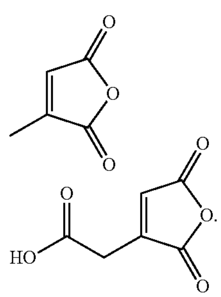

4. The polymer complex according to claim 1, wherein the cationic polymer is any compound selected from the group consisting of:

a compound of Formula (2):

(2)

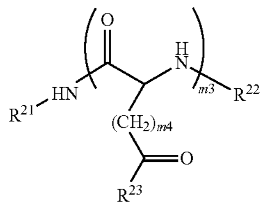

wherein $R^{21}$ and $R^{22}$ independently represent a hydrogen atom or an optionally substituted linear or branched alkyl group with a carbon number of 1-12, $R^{23}$ represents a group of Formula (22):

$$—NH—(CH_2)_r—X^{21} \quad (22)$$

wherein $X^{21}$ is a group selected from $—NH_2$, $—NH—CH_3$, $—N(CH_3)_2$ and a group represented by one of Formulas (i)-(viii):

(i)

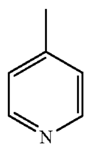

(ii)

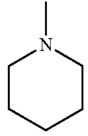

(iii)

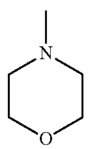

(iv)

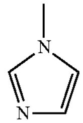

(v)

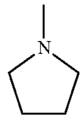

(vi)

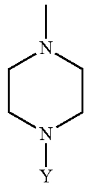

-continued (vii)

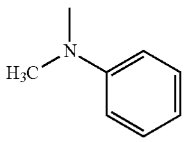

(viii)

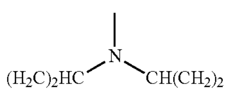

and r represents a integer of 0-5; or a group of General Formula (23):

$$—[NH—(CH_2)_{s2}]_{t2}—X^{22} \quad (23)$$

wherein $X^{22}$ has the same definition as $X^{21}$, and s2 and t2, independently from each other and independently between the $[NH—(CH_2)_{s2}]$ units, represent integers of 1-5 and 2-5, respectively, m3 represents an integer of 10-500, and m4 represents an integer of 1-5;

a compound of Formula (3):

(3)

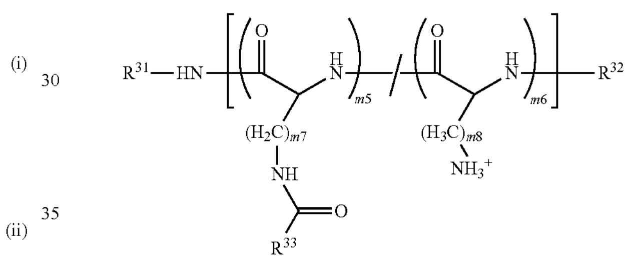

wherein $R^{31}$ and $R^{32}$ are synonymous with $R^{21}$ and $R^{22}$, respectively, $R^{33}$ represents an optionally substituted saturated or unsaturated linear or branched aliphatic hydrocarbon group or steroloxycarbonyl group with a carbon number of 11-27, m5 and m6 independently represent an integer of 0-500, provided that the sum of m5 and m6 is an integer of 10-500, m7 represents an integer of 1-5, m8 represents an integer of 1-5, and the sign "/" indicates that the sequential order of the (m5+m6) numbers of monomer units on both sides of the sign are arbitrary;

a compound of Formula (4):

(4)

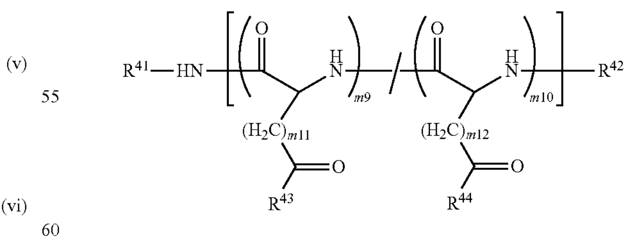

wherein $R^{41}$ and $R^{42}$ are synonymous with $R^{21}$ and $R^{22}$, respectively, $R^{43}$ is synonymous with $R^{33}$, $R^{44}$ is synonymous with $R^{23}$, m9 and m10 are synonymous with m5 and m6, respectively, m11 and m12 are synonymous with m7 and m8, respectively, and the sign "/" is synonymous with the same above; and a compound of Formula (5):

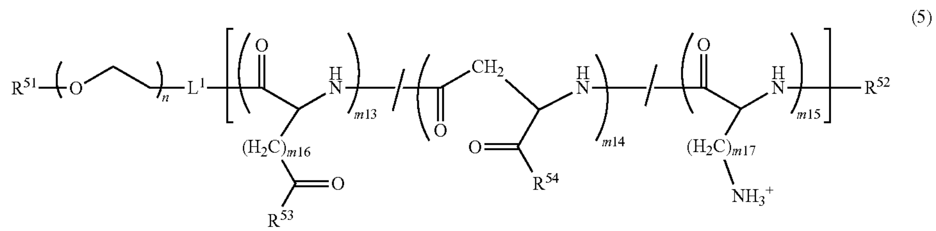

wherein $R^{51}$ and $R^{52}$ are synonymous with $R^{21}$ and $R^{22}$, respectively, $R^{53}$ and $R^{54}$ are synonymous with $R^{23}$, $L^{1}$ represents NH, CO, a group of General Formula (13):

$$—(CH_2)_{p1}—NH— \quad (13)$$

wherein p1 represents an integer of 1-6, or a group represented by the following General Formula (14):

$$-L^{2a}-(CH_2)_{q1}-L^{3a}- \quad (14)$$

wherein $L^{2a}$ represents OCO, OCONH, NHCO, NHCOO, NHCONH, CONH or COO, $L^{3a}$ represents NH or CO, and q1 represents an integer of 1-6, m13, m14 and m15 independently represent an integer of 0-500, provided that the sum of m13, m14 and m15 is an integer of 10-500, m16 and m17 are synonymous with m7 and m8, respectively, n represents an integer of 0-500, and the sign "/" indicates that the sequential order of the (m13+m14+m15) numbers of monomer units on both sides of the sign are arbitrary.

5. A device for delivering a nucleic acid into a cell, comprising the polymer complex according to claim 1.

6. A kit for delivering a nucleic acid into a cell, comprising the polymer complex according to claim 1.

7. A device for delivering a nucleic acid into a cell, comprising the polymer complex according to claim 2.

8. A kit for delivering a nucleic acid into a cell, comprising the polymer complex according to claim 2.

9. A device for delivering a nucleic acid into a cell, comprising the polymer complex according to claim 3.

10. A kit for delivering a nucleic acid into a cell, comprising the polymer complex according to claim 3.

11. The polymer complex according to claim 1, wherein the anionic polymer covers the surface of a complex comprising the cationic polymer and the nucleic acid.

* * * * *